United States Patent
Stamler et al.

(10) Patent No.: US 6,203,789 B1
(45) Date of Patent: Mar. 20, 2001

(54) RED BLOOD CELLS LOADED WITH S-NITROSOTHIOL AND USES THEREFOR

(75) Inventors: Jonathan S. Stamler, Chapel Hill; Joseph Bonaventura, Durham, both of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/873,679

(22) Filed: Jun. 12, 1997

Related U.S. Application Data

(63) Continuation-in-part of application No. PCT/US96/14664, filed on Sep. 13, 1996, which is a continuation-in-part of application No. 08/616,255, filed on Mar. 15, 1996.
(60) Provisional application No. 60/003,801, filed on Sep. 15, 1995.

(51) Int. Cl.[7] .................................................. C12N 5/08

(52) U.S. Cl. ...................... 424/93.73; 424/93.7; 435/372

(58) Field of Search ................................ 424/93.7, 93.73; 435/372

(56) References Cited

U.S. PATENT DOCUMENTS

| | | | |
|---|---|---|---|
| 4,900,719 | 2/1990 | Means et al. | 514/18 |
| 5,380,758 | 1/1995 | Stamler et al. | 514/562 |
| 5,405,919 | 4/1995 | Keefer et al. | 525/377 |
| 5,427,797 | 6/1995 | Frostell et al. | 424/434 |
| 5,480,866 | 1/1996 | Bonaventura et al. | 514/6 |
| 5,574,068 | 11/1996 | Stamler et al. | 514/562 |
| 5,593,876 | 1/1997 | Stamler et al. | 435/188 |

FOREIGN PATENT DOCUMENTS

| | | |
|---|---|---|
| 0604143 | 6/1994 | (EP) . |
| WO 93/09806 | 5/1993 | (WO) . |
| WO 93/12068 | 6/1993 | (WO) . |
| WO 94/22306 | 10/1994 | (WO) . |
| WO 94/22482 | 10/1994 | (WO) . |
| WO 94/22499 | 10/1994 | (WO) . |
| WO 96/15797 | 5/1996 | (WO) . |
| WO 96/16645 | 6/1996 | (WO) . |
| WO 96/17604 | 6/1996 | (WO) . |
| WO 96/30006 | 10/1996 | (WO) . |

OTHER PUBLICATIONS

Kruszyna, H. et al., "Red Blood Cells Generate Nitric Oxide From Directly Acting, Nitrogenous Vasodilators," *Toxicology and Applied Pharmacology,* 91:429–438 (1987).

Stamler, Jonathan S. et al., "S–Nitrosylation of Proteins with Nitric Oxide: Synthesis and Characterization of Biologically Active Compounds," *Proc. Natl. Acad. Sci. USA,* 89:444–448 (1992).

Langford, E.J. et al., "Inhibition of Platelet Activity by S–Nitrosoglutathione During Coronary Angioplasty," *The Lancet,* 344:1458–1460 (1994).

Ribeiro, José M.C. et al., "Reversible Binding of Nitric Oxide by a Salivary Heme Protein from a Bloodsucking Insect," *Science,* 260:539–541 (1993).

Olsen, Stephen B. et al., "Enhancement of Platelet Deposition by Cross–Linked Hemoglobin in a Rat Carotid Endarterectomy Model," *Circulation,* 93(2):327–332 (1996).

Scharfstein, Jonathan S. et al., "In Vivo Transfer of Nitric Oxide Between a Plasma Protein–Bound Reservoir and Low Molecular Weight Thiols," *J. Clin. Invest.,* 94:1432–1439 (1994).

Charache, S. et al., "Evaluation of Extracorporeal Alkylation of Red Cells as a Potential Treatment for Sickel Cell Anemia," *Blood,* 47(3):481–488 (1976).

Kosaka, Hiroaki et al., "ESR Spectral Transition by Arteriovenous Cycle in Nitric Oxide Hemoglobin of Cytokine–Treated Rats," *Am. J. Physiol.,* 266(5):1400–1405 (1994).

Doyle, Michael P. et al., "Structural Effects in Alkyl Nitrite Oxidation of Human Hemoglobin," *Journal of Biological Chemistry,* 259(1):80–87 (1984).

Greenburg, A.G. and Kim, H.W., "Nitrosyl Hemoglobin Formation In–Vivo After Intravenous Administration of a Hemoglobin–Based Oxygen Carrier in Endotoxemic Rats." *Artif. Cells, Blood Substitutes, Immobilization Biotechnol.,* 23(3):271–276 (1995).

Stamler, Jonathan S., "Redox Signaling: Nitrosylation and Related Target Interactions of Nitric Oxide," *Cell* 78:931–936 (1994).

Arnelle, Derrick R. and Stamler, Jonathan S., "$NO^+$, $NO^-$, and $NO^-$ Donation by S–Nitrosothiols: Implications for Regulation of Physiological Functions by S–Nitrosylation and Acceleration of Disulfide Formation," *Archives of Biochemistry and Biophysics,* 318(2):279–285 (1995).

Kondo, T. et al., "Thiol Transport from Human Red Blood Cells," *Methods in Enzymology,* 252:72–82 (1995).

Freelisch, M. and Stamler, J.S., "Donors of Nitrogen Oxides," *Methods In Nitric Oxide Research,* John Wiley & Sons Ltd. (1996).

Stamler, J.S. and Feelisch, M., "Preparation and Detection of S–Nitrosothiols," *Methods in Nitric Oxide Research,* John Wiley & Sons Ltd. (1996).

Clancy, R.M. et al., "Nitric Oxide Reacts with Intracellular Glutathione and Activates the Hexose Monophosphate Shunt in Human Neutrophils: Evidence for S–Nitrosogluthathione as a Bioactive Intermediary," *Proc. Natl. Acad. Acad. Sci. USA,* 91:3680–3684 (1994).

(List continued on next page.)

*Primary Examiner*—Jean C. Witz
(74) *Attorney, Agent, or Firm*—Hamilton, Brook, Smith & Reynolds, P.C.

(57) ABSTRACT

Red blood cells can be loaded with low molecular weight nitrosylating agents, such as S-nitrosothiols, to act as a delivery system for $NO^+$ groups to tissues. Loaded red blood cells can be used in methods of therapy for conditions which are characterized by abnormal $O_2$ metabolism of tissues, oxygen-related toxicity, abnormal vascular tone, abnormal red blood cell adhesion, or abnormal $O_2$ delivery by red blood cells.

11 Claims, 15 Drawing Sheets

Ignarro, Louis J. et al., "Mechanism of Vascular Smooth Muscle Relaxation by Organic Nitrates, Nitrites, Nitroprusside and Nitric Oxide: Evidence for the Involvement of S–Nitrosothiols as Active Intermediates," *The Journal of Pharmacology and Experimental Therapeutics,* 218 (3):739–749 (1981).

Simon, Daniel I. et al., "Effect of Nitric Oxide Synthase Inhibition on Bleeding Time in Humans," *Journal of Cardiovascular Pharmacology,* 26:339–342 (1995).

Kumura, Eiji et al., "Nitrosyl Hemoglobin Production During Reperfusion After Focal Cerebral Ischemia in Rats," *Neuroscience Letters,* 177:165–167 (1994).

Jia, Li et al., "S–Nitrosohaemoglobin: A Dynamic Activity of Blood Involved in Vascular Control," *Nature,* 380:221–226 (1996).

Shiga, Takeshi et al., "Electron Paramagnetic Resonance Studies of Nitric Oxide Hemoglobin Derivatives: I. Human Hemoglobin Subunits," *Biochemistry,* 8:378–383 (1969).

Garel, Marie Claude et al., "Binding of 21 Thiol Reagents to Human Hemoglobin in Solution and in Intact Cells," *Eur. J. Biochem.,* 123:513–519 (1982).

Garel, Marie–Claude et al., "Covalent Binding of Glutathione to Hemoglobin: I. Inhibition of Hemoglobin S Polymerization," *The Journal of Biological Chemistry,* 261(31):14704–14709 (1986).

Wennmalm, Å et al., "Dependence of the Metabolism of Nitric Oxide (NO) in Healthy Human Whole Blood on the Oxygenation of Its Red Cell Haemoglobin," *Br. J. Pharmacol.,* 106:507–508 (1992).

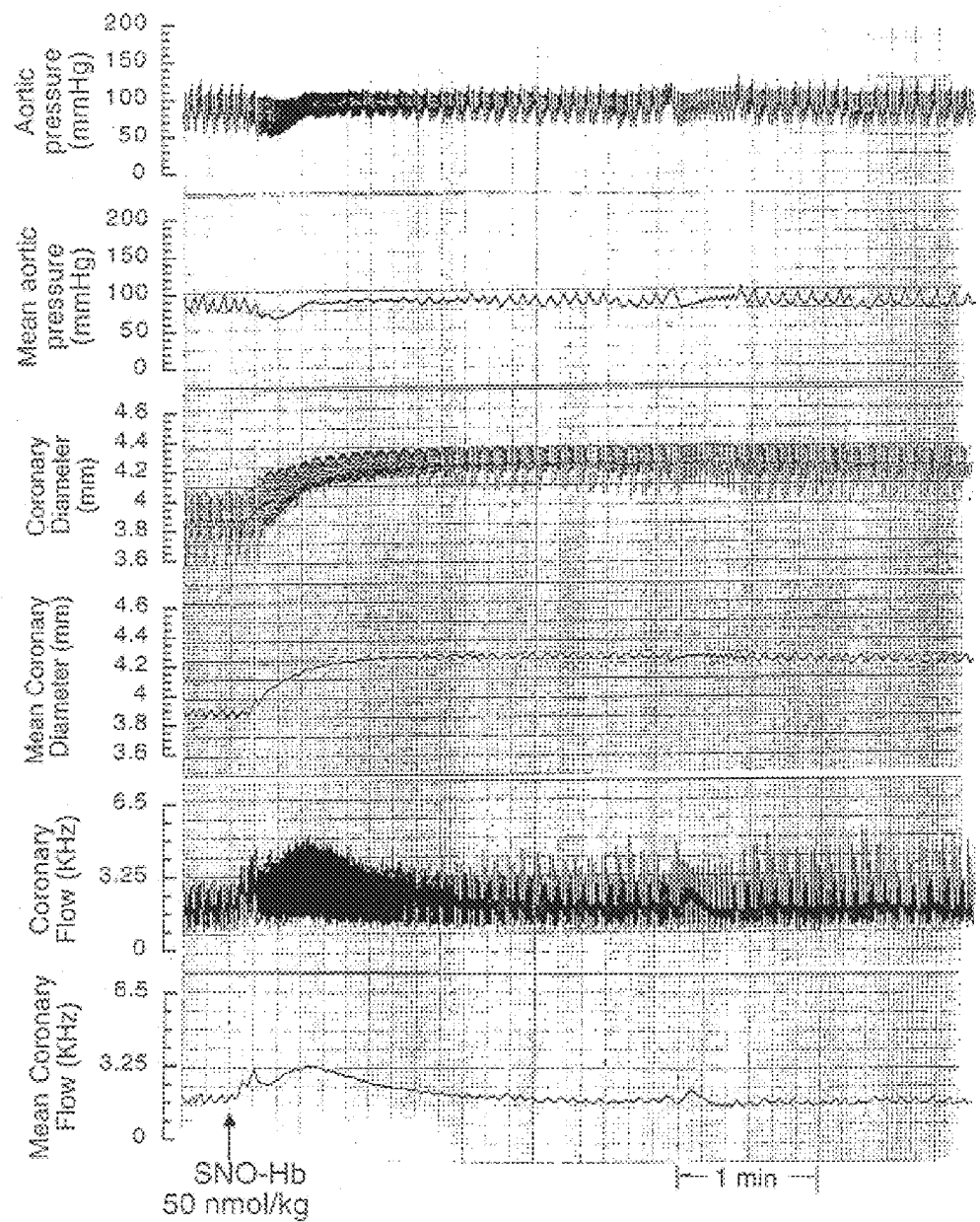

RED BLOOD CELLS LOADED WITH S-NITROSOTHIOL AND USES THEREFOR

RELATED APPLICATIONS

This application is a continuation-in-part of PCT/US96/14664 filed on Sep. 13, 1996, which is a continuation of U.S. application Ser. No. 08/616,255 filed on Mar. 15, 1996, which claims priority to U.S. Provisional Application No. 60/003,801 filed on Sep. 15, 1995. The teachings of all of the above applications are each incorporated herein by reference in their entirety.

GOVERNMENT SUPPORT

This invention has made with Government support under Grant No. HL52529 awarded by the National Institutes of Health. The Government has certain rights in the invention.

BACKGROUND OF THE INVENTION

Interactions of hemoglobin (Hb) with small diffusible ligands, such as $O_2$, $CO_2$ and NO, are known to occur at its metal centers and amino termini. The $O_2/CO_2$ delivery functions, which arise in the lung and systemic microvasculature, are allosterically controlled. Such responsiveness to the environment: has not been known to apply in the case of NO. Specifically, it has been thought previously that NO does not modify the functional properties of Hb to any physiologically significant degree. Kinetic modeling predicts that the vast majority of free NO in the vasculature should be scavenged by Hb (Lancaster 1994). Accordingly, the steady-state level of NO may fall below the $K_m$ for target enzymes such as guanylate cyclase (Lancaster 1994), if not in the unperturbed organism, then with oxidant stress such as that found in atherosclerosis. These considerations raise the fundamental question of how NO exerts its biological activity.

One answer to this question is found in the propensity of nitric oxide to form S-nitrosothiols (RSNOs) (Gaston, B. et al., *Proc. Natl. Acad. Sci. USA* 90:10957–10961 (1993)), which retain NO-like vasorelaxant activity (Stamler, J. S., et al., *Proc. Natl. Acad. Sci. USA* 89:444–448 (1992)), but which can diffuse freely in and out of cells, unlike Hb. In particular, the NO group of RSNOs possesses nitrosonium ($NO^+$) character that distinguishes it from NO itself. It is increasingly appreciated that RSNO's have the capacity to elicit certain functions that NO is incapable of (DeGroote, M. A. et al., *Proc. Natl. Acad. Sci. USA* 92:6399–6403 (1995); Stamler, J. S., *Cell* 78:931–936 (1994)). Moreover, consideration has been given to the possibility that —SNO groups in proteins serve a signaling function, perhaps analagous to phosphorylation (Stamler, J. S. et al., *Proc. Natl. Acad. Sci. USA* 89:444–448 (1992); Stamler, J. S. *Cell* 78:931–926 (1994)). Although S-nitrosylation of proteins can regulate protein function (Stamler, J. S. et al., *Proc. Natl. Acad. Sci. USA* 89:444–448 (1992); Stamler, J. S., *Cell* 78:931–936 (1994)), the identification of S-nitrosoproteins within cells—the sine qua non of a regulatory posttranslational modification—has heretofore not been demonstrated.

Hemoglobin is a tetramer comprised of two alpha and two beta subunits. In human Hb, each subunit contains one heme, while the beta (β) subunits also contain highly reactive SH groups (cysoβ93) (Olson, J. S., *Meth. in Enzym.* 76:631–651 (1981); Antonini & Brunori, *In Hemoglobin and Myoglobin in Their Reactions with Ligands,* American Elsevier Publishing Co., Inc., New York, pp. 29–31 (1971)). These cysteine residues are highly conserved among species although their function has remained elusive.

NO (nitric oxide) is a biological "messenger molecule" which decreases blood pressure and inhibits platelet function, among other functions. NO freely diffuses from endothelium to vascular smooth muscle and platelet and across neuronal synapses to evoke biological responses. Furthermore, under some conditions, reactions of NO with other components present in cells and in body fluids can generate toxic intermediates and products at local concentrations in tissues which are effective at inhibiting the growth of infectious organisms. Thus, it can be seen that a method of administering an effective concentration of NO or biologically active forms thereof would be beneficial in certain medical disorders.

SUMMARY OF THE INVENTION

The invention relates to a method for the extracorporeal loading of red blood cells (RBCs) with a low molecular weight reagent which is capable of entering the red blood cells and causing S-nitrosylation at thiol groups. S-nitrosothiols such as S-nitrosocysteine, and related peptides can be used to load red blood cells, which can then be introduced into a mammal. The red blood cells thereby become carriers of NO. In this manner, medical conditions characterized by abnormal oxygen metabolism of tissues, oxygen-related toxicity, abnormal vascular tone, abnormal red blood cell adhesion, or abnormal $O_2$ delivery by red blood cells, can be treated.

BRIEF DESCRIPTIONS OF THE DRAWINGS

FIGS. 6A–6F are a series of tracings recording blood pressure (FIGS. 6A and 6B), coronary artery diameter (FIGS. 6C and 6D) and coronary artery flow (FIGS. 6E and 6F), after administration of S-nitrosohemoglobin to anesthetized dogs.

Figure 7A:
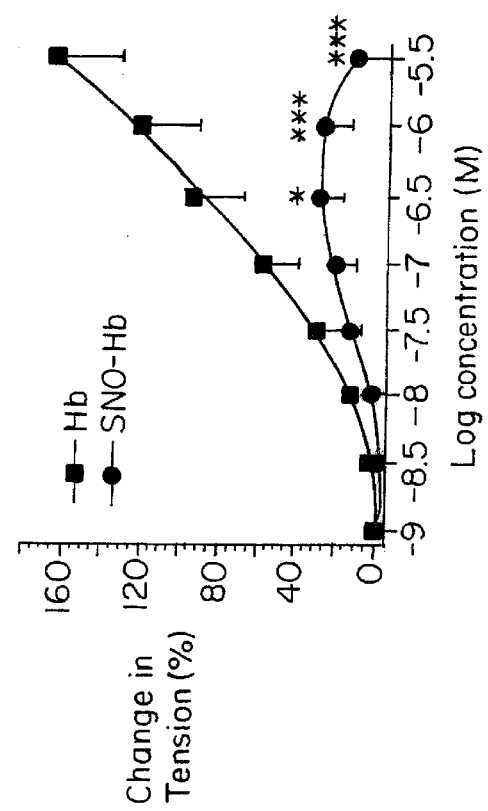
Figure 7B:
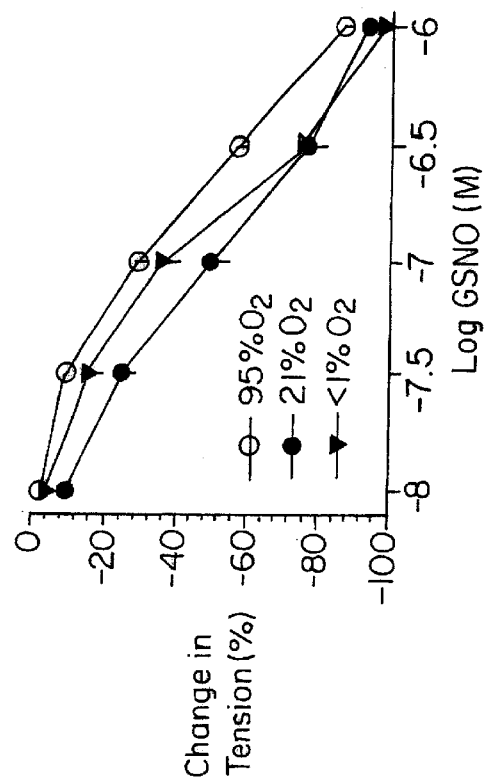

FIGS. 7A and 7B are graphs showing the contractile effects of oxyHb, SNO-oxyHb, deoxy-Hb and SNO-deoxy-Hb on thoracic aortic ring isolated from rabbit. Measurements are shown as percent increase in tension of aortic ring as a function of the log of the concentration of hemoglobin or SNO-hemoglobin. Measurements were made after the tension had stabilized.

Figure 7C:
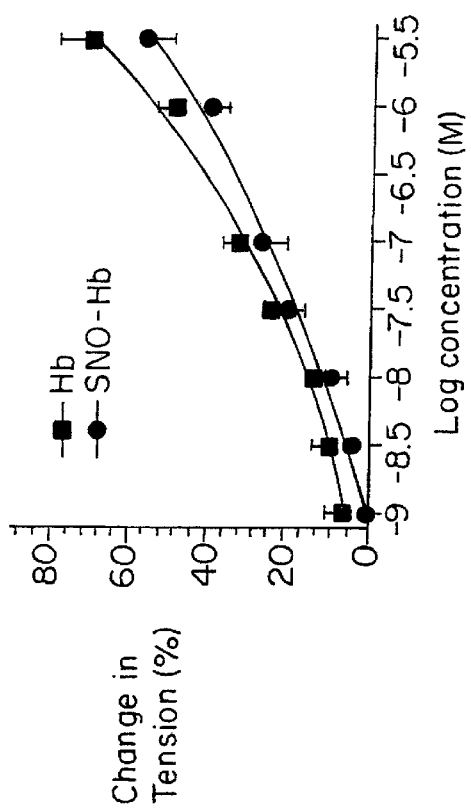

FIG. 7C is a graph showing the percent change in tension of contracted aortic ring as a function of the log concentration of SNO-hemoglobin at the concentrations of $O_2$ indicated, in addition to 10 μM glutathione.

Figure 7D:
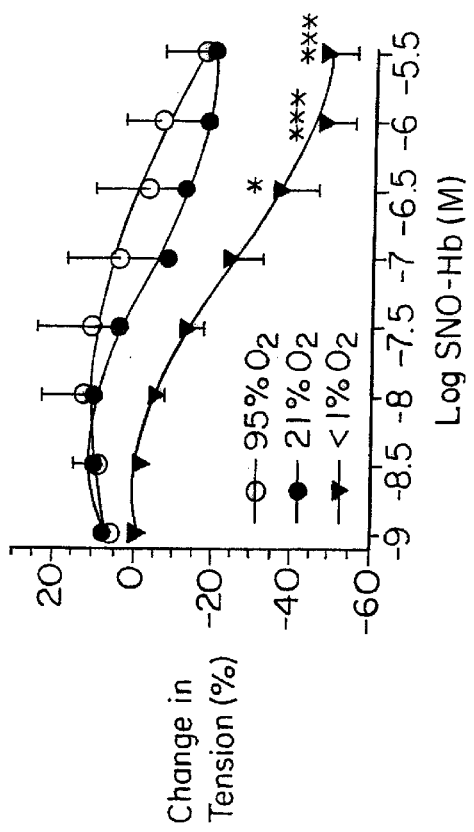

FIG. 7D is a graph showing the percent change in tension of contracted aortic ring as a function of the log concentration of SNO-glutathione, in the concentrations of $O_2$ indicated.

Figure 8A:
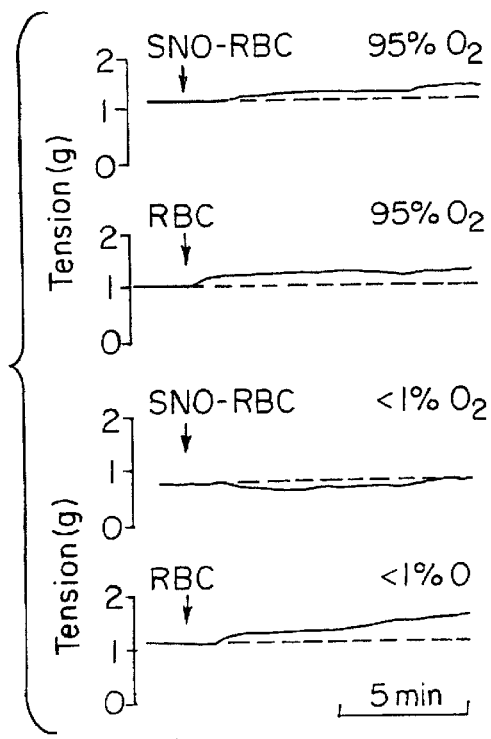
Figure 8B:
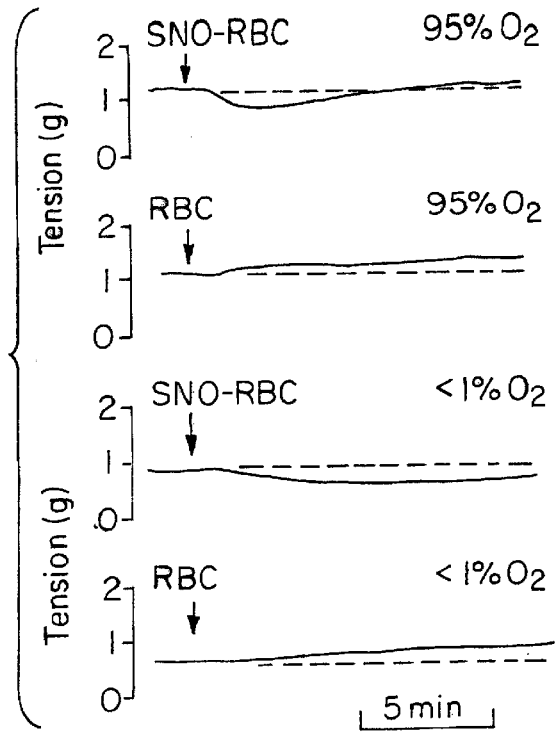

FIG. 8A and FIG. 8B are each a series of four graphs illustrating the change with time in tension of rabbit aortic ring upon the addition of red blood cells treated with S-nitrosocysteine ("red blood cells loaded with nitric oxide"), or untreated red blood cells, as indicated, in the concentration of $O_2$ indicated.

Figure 8C:
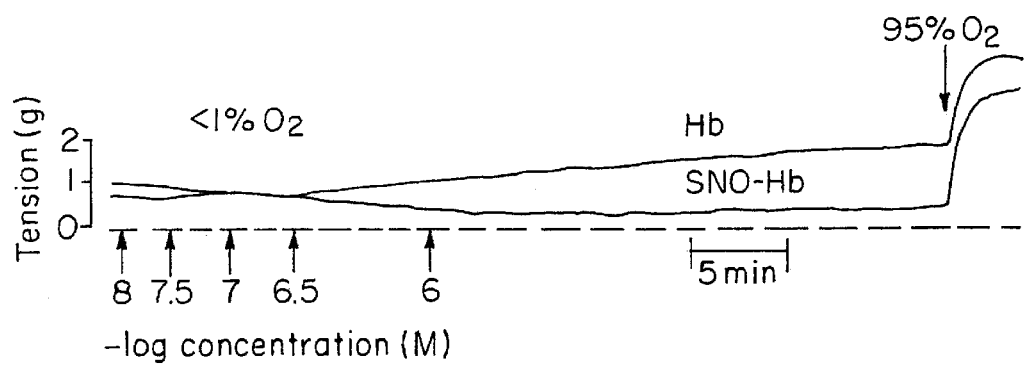

FIG. 8C is a graph illustrating the change with time in tension of rabbit aortic ring contracted with phenylephrine under hypoxic conditions (6–7 torr) and then exposed to either 1 μM Hb or SNO-Hb.

Figure 9:
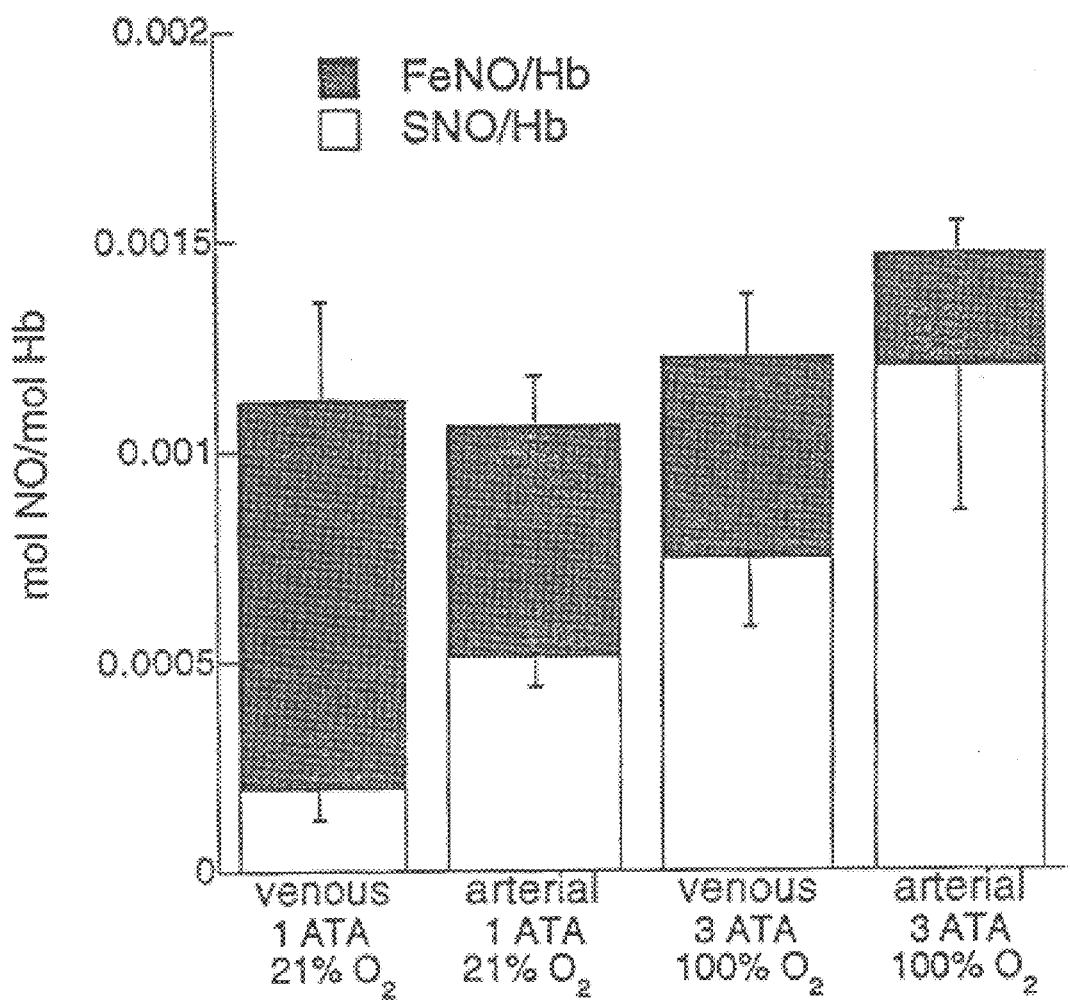
Figure 10A:
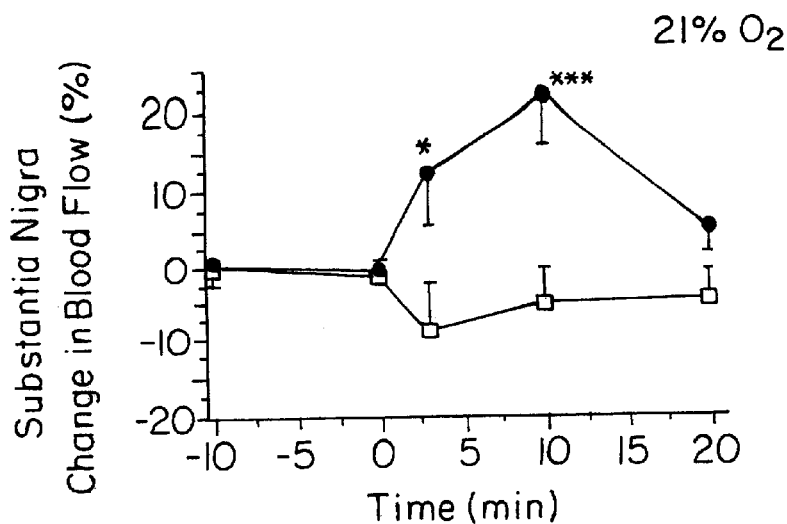
Figure 10B:
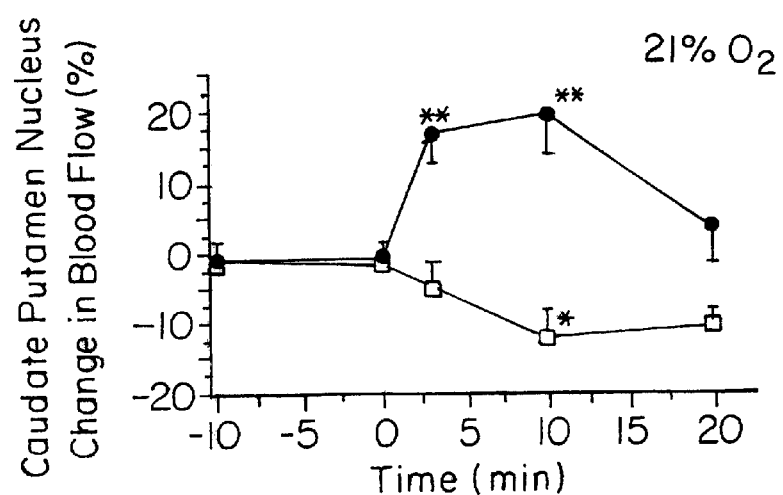
Figure 10C:
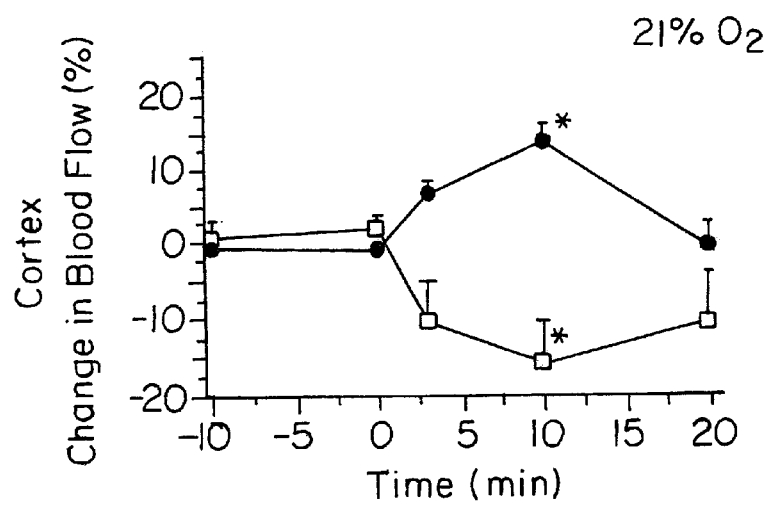
Figure 10D:
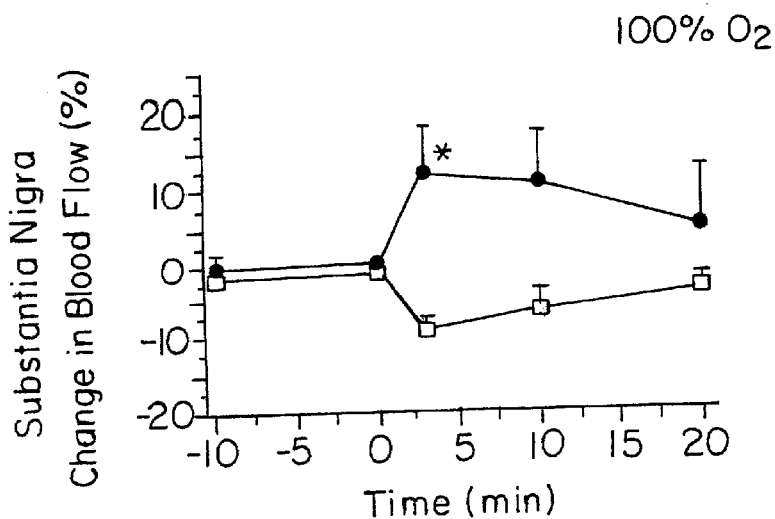
Figure 10E:
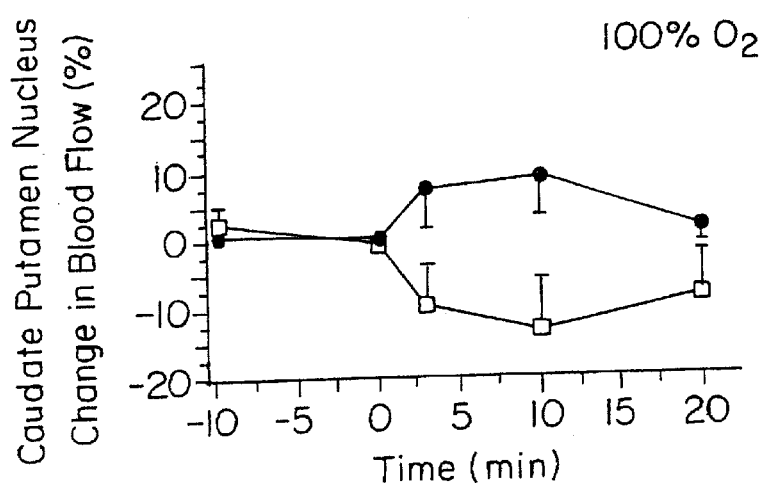
Figure 10F:
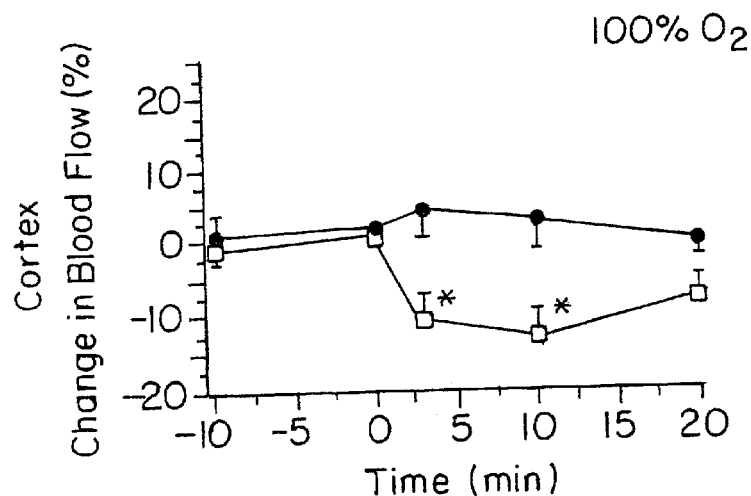
Figure 10G:
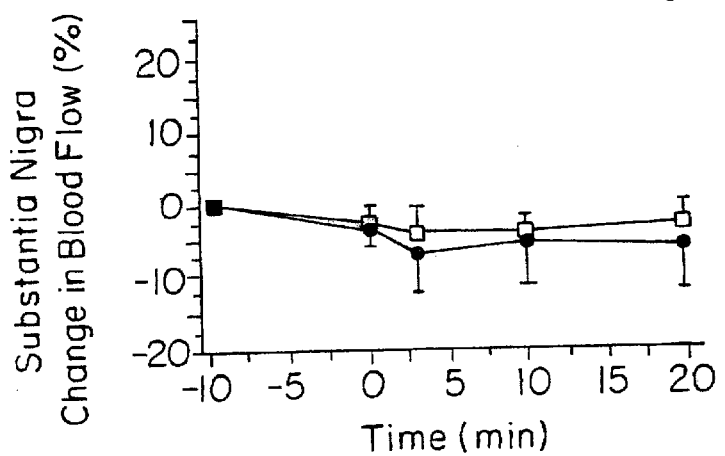
Figure 10H:
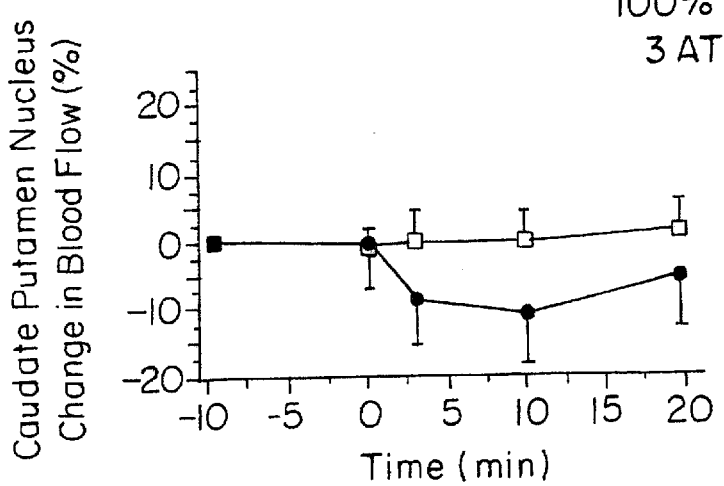
Figure 10I:
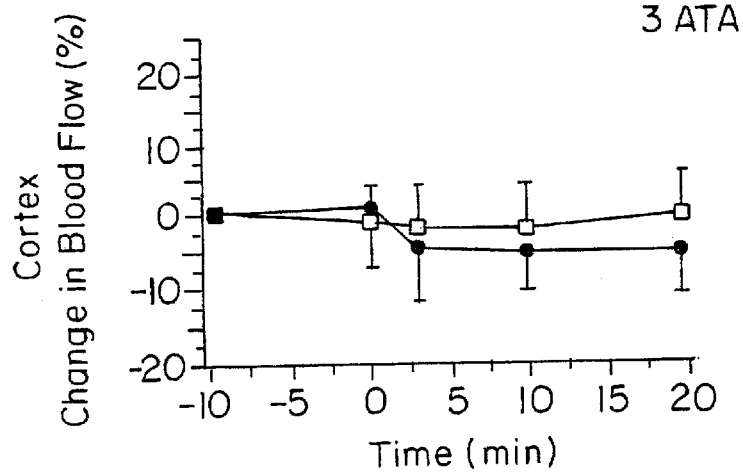

FIG. 9 is a bar graph depicting the concentrations of FeNO/Hb and SNO/Hb in venous or arterial blood as measured in Example 11. ATA=atmospheres of absolute pressure.

FIGS. 10A–10I are each a graph showing the effects of SNO-Hb (●) and Hb (■) (1 μmol/kg infused over 3 minutes) on local blood flow in substantia nigra (SN), caudate putamen nucleus, and parietal cortex of rats, in 21% $O_2$ (FIGS. 10A, 10B and 10C), in 100% $O_2$ (FIGS. 10D, 10E and 10F) and in 100% $O_2$ at 3 atmospheres absolute pressure (FIGS. 10G, 10H and 10I) as measured in Example 12.

Figures 11A, 11B:
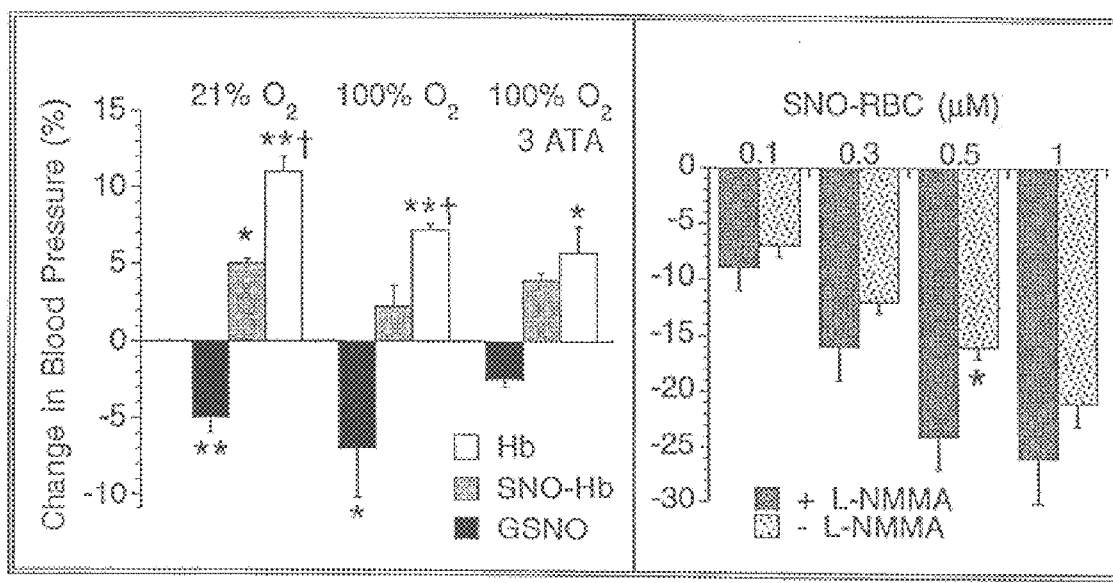

FIG. 11A is a bar graph showing the percent change in blood pressure of rats, during exposure to three different conditions (inspired $O_2$ concentrations of 21%, 100%, or 100% $O_2$ at 3 ATA) upon infusion of GSNO, SNO-Hb, or Hb, as tested in Example 13.

FIG. 11B is a bar graph showing the percent change in blood pressure of rats [pre-administered (+L-NMMA), or not preadministered (−L-NMMA), $N^G$-monomethyl-L-arginine] upon infusion of SNO-RBCs, as tested in Example 13.

DETAILED DESCRIPTION OF THE INVENTION

Roles for Hemoglobin in Physiology

The increase in SNO-Hb content of red cells across the pulmonary circuit (right ventricular inport-left ventricle) suggests that the Hb molecule is S-nitrosylated in the lung. Selective transfer of the NO group from endogenous RSNOs found in lung (Gaston, et al. (1993)) and blood (Scharfstein, J. S. et al., *J. Clin. Invest.* 94:1432–1439 (1995)) to SH groups of Hb, substantiate these findings. The corresponding decline in Hb(FeII)NO levels across the pulmonary bed reveals a role for the lung either in the elimination of NO or in its intramolecular transfer from heme to cysβ93. Taken in aggregate, these data extend the list of function-regulating interactions of Hb with small molecules within the respiratory system, previously known to include the elimination of CO and $CO_2$, and uptake of $O_2$. Since, as demonstrated herein, oxygenation of Hb leads to structural changes that increase the NO-related reactivity of cysβ93, $O_2$ can now be regarded as an allosteric effector of Hb S-nitrosylation.

The arterial-venous difference in SNO-Hb concentration suggests that the protein acts as an NO group donor in the systemic circulation. There is good indication that SNO-Hb functions in regulation of vasomotor tone. In the microcirculation, where control of blood pressure is achieved, erythrocytes come in intimate contact with endothelial surfaces. Under these conditions, Hb can contract the vasculature by sharply decreasing the steady state level of free NO (Lancaster, J. R., (1994)). This is believed to contribute to the increases in blood pressure that occur with infusion of cell-free Hbs (Vogel, W. M., et al., *Am. J. Physiol.* 251:H413–H420 (1986); Olsen, S. B., et al., *Circulation* 93:329–332 (1996)). The transient nature of such hypertensive responses, however, is consistent with the subsequent formation of SNO-Hb which counteracts this effect, evidenced by its lowering of blood pressure at naturally occurring concentrations. Thus, the capacity of the erythrocyte to support the synthesis and metabolism of SNO-Hb is important for normal blood flow.

Figure 1A:
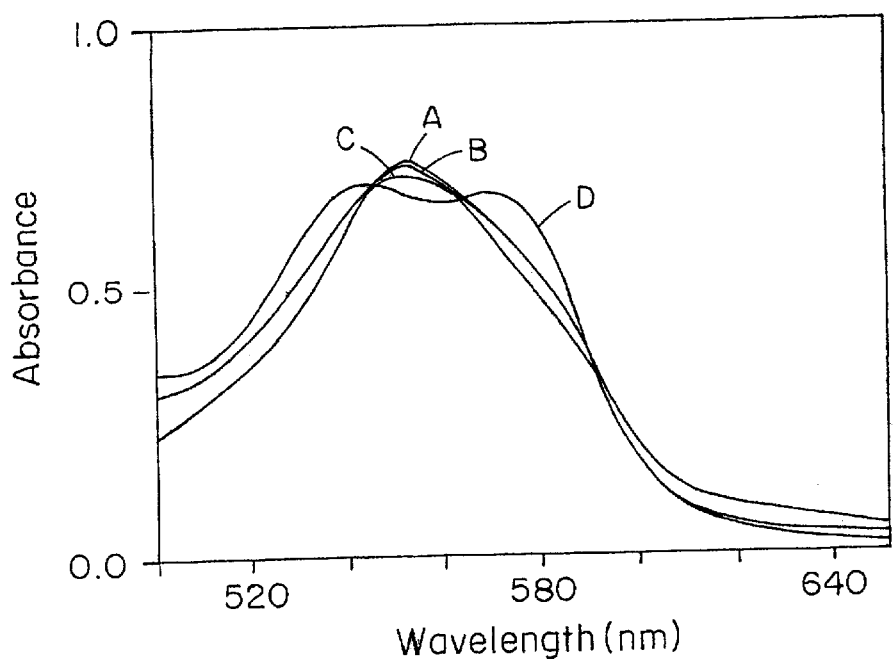
FIGS. 1A–1D are spectrographs of different forms of Hb as described in Example 1.
Figure 1B:
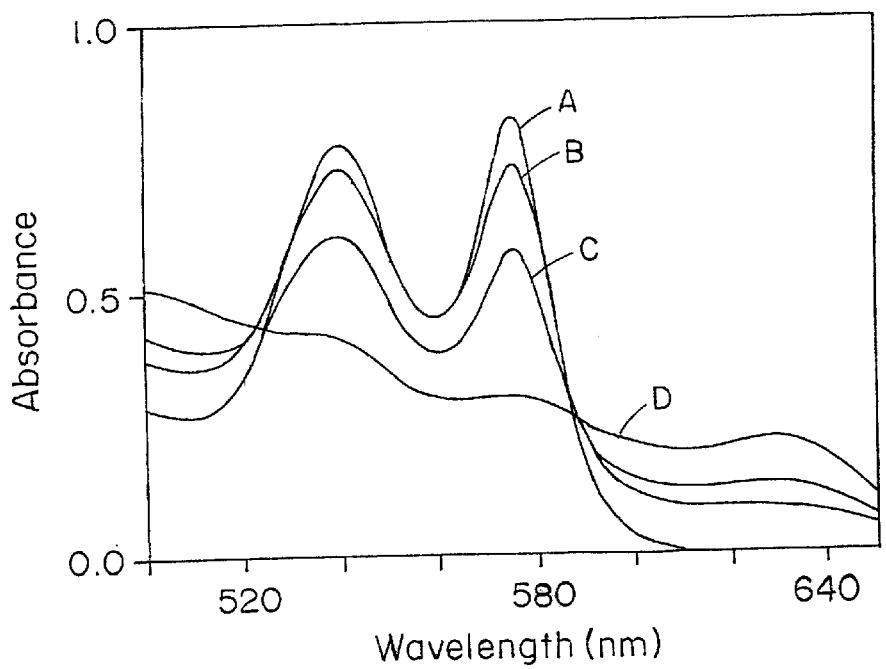
Figure 3A:
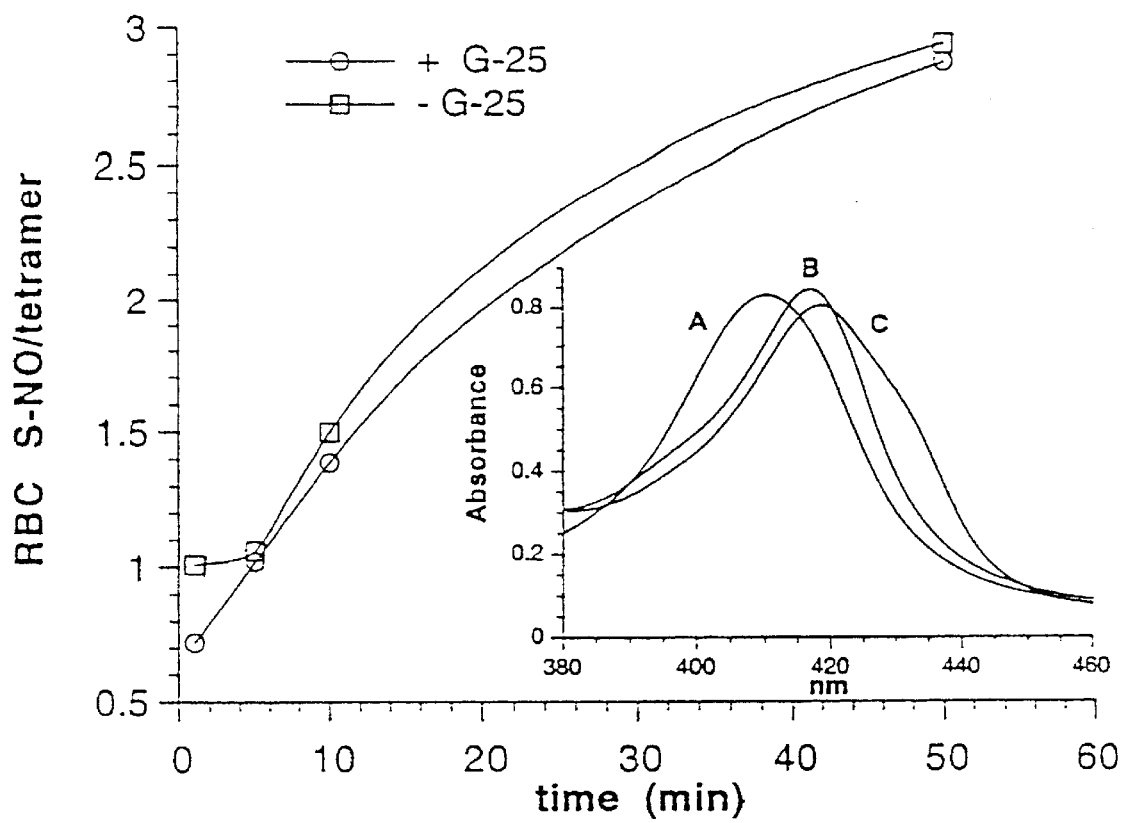
FIG. 3A is a graph showing the loading of red blood cells with S-nitrosocysteine, over time. The inset is a series of spectrographs of forms of Hb as described in Example 3.
Figure 3B:
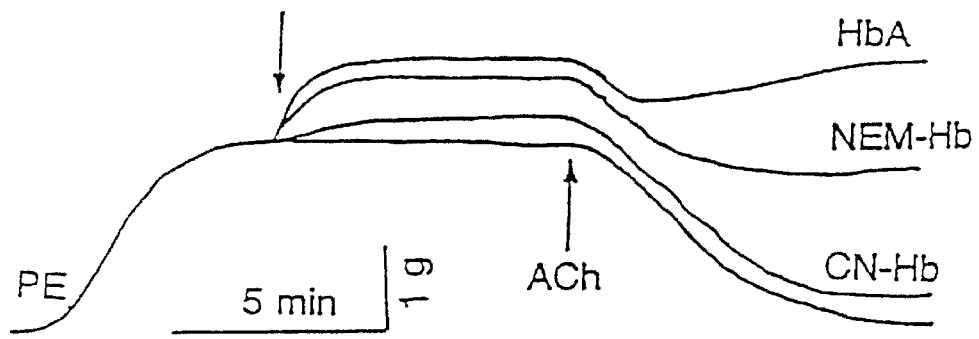
FIG. 3B is a series of tracings recording isometric tone of a rabbit aortic ring following treatment of the aortic ring with various agents as described in Example 3.
Figure 4A:
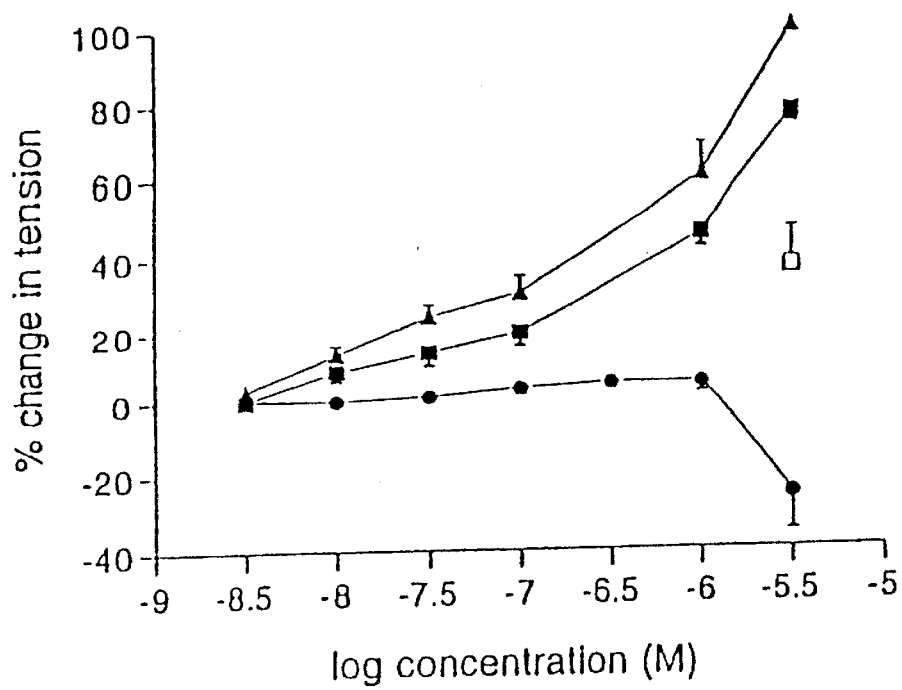
FIG. 4A is a graph of change in tension of a rabbit aortic ring versus concentration of the Hb used in the experiment.

Mammals must have adopted unique molecular mechanisms to ensure adequate NO delivery in the microcirculation. Results herein suggest that Hb has evolved both electronic and conformational switching mechanisms to achieve NO homeostasis. Specifically, NO scavenging by the metal center(s) of SNO-Hb(FeII)$O_2$ is sensed through its conversion to met(FeIII) (FIG. 1B). This electronic switch effects decomposition of SNO-Hb with NO group release (FIGS. 3A, 3B, 4A). In this manner, the NO-related activity of SNO-Hb is partly determined by the amount of NO scavenged. Changes in $O_2$ tension also function to regulate NO delivery, as it is observed herein that NO release is facilitated by deoxygenation. This allosteric effect promotes the efficient utilization of $O_2$, as NO controls mitochondrial respiration (Shen, W., et al., *Circulation* 92:3505–3512 (1995)).

S-nitrosothiol groups in proteins have been implicated in NO metabolism and in regulation of cellular functions (Stamler, J. S., et al., *Proc. Natl. Acad. Sci USA* 89:444–448 (1992); Stamler, J. S., *Cell* 78:931–936 (1994)). The identification of SNO-Hb in erythrocytes is the first demonstration of an intracellular S-nitrosoprotein and gives further credence to the role of such proteins in cellular regulation. The question arises as to how SNO-Hb relaxes blood vessels when any free NO released would be scavenged instantaneously by Hb itself, according to previous theories (Lancaster, J. R., (1994)). Noteworthy in this regard are studies showing that RSNO activity involves nitrosyl ($NO^+$) transfer to thiol acceptors (Scharfstein, J. S., et al., (1994); Arnelle, D. R. and Stamler, J. S., *Arch. Biochem. Biophys.* 318:279–285 (1995); Stamler, J. S., et al., *Proc. Natl. Acad. Sci. USA* 89:7674–7677 (1992)), which serve to protect the NO-related activity from inactivation at metal centers. Findings presented herein indicate that S-nitrosothiol/thiol exchange with glutathione (forming GSNO) occurs within erythrocytes, and is influenced by the oxidation state of heme and its occupation by ligand. Certain activities of GSNO in bacteria require transport of intact dipeptide (i.e., S-nitrosocysteinylglycine) across the cell membrane (DeGroote, M. A., et al., *Proc. Natl. Acad. Sci. USA* 92:6399–6403 (1995)). The data presented below in the Examples show that S-nitrosothiol transport occurs also in eukaryotic cells. GSNO, or related thiol carriers exported by erythrocytes (Kondo, T., et al., *Methods in Enzymology*, Packer, L., ed., Academic Press, 252:72–83 (1995)), might also initiate signalling in or at the plasmalemma (Stamler, J. S., *Cell* 78:931–936 (1994)), given reports of thiol-dependent activation of potassium channels by EDRF (Bolotina, V. M., et al., *Nature* 368:850–853 (1994)). Alternative possibilities also merit consideration. In particular, reports that Hb associates with red cell membranes via cysβ93 (Salhany, J. M. and Gaines, K. C., *Trends in Biochem. Sci.*, pp. 13–15, Janurary (1981)) places Hb in a position to donate the NO group directly to contacting endothelial surfaces, perhaps via SNOiSH exchange. Cell surface interactions appear to be operative in signaling mediated by other S-nitrosoproteins (Stamler, J. S., et al., *Proc. Natl. Acad. Sci. USA* 89:444–448 (1992); Stamler, J. S., *Cell* 78:931–936 (1994)).

The highly conserved Cysβ93 residues in Hb influence the oxygen affinity and redox potential of the heme iron and its physiochemical properties (Garel, C., et al., *Biochem.* 123:513–519 (1982); Jocelyn, P. C., et al., *Biochemistry of the SH Group*, p. 243, Academic Press, London; (1972); Craescu, C. T., *J. Biol. Chem.* 261:14710–14716 (1986); Mansouri, A., *Biochem. Biophys. Res. Commun.* 89:441–447 (1979)). Nonetheless, their long sought-after physiological function has remained a mystery. The studies herein suggest new sensory and regulatory roles for Hb, in which Cysβ93 functions in transducing NO-related signals to the vessel wall. In particular, the physiological function of Cysβ93, which is invariant in all mammals and birds, is to deliver under allosteric control, NO-related biological activity that cannot be scavenged by heme. Thus, these data bring to light a dynamic circuit for the NO group in which intraerythrocytic Hb participates as both a sink and a donor, depending on its microenvironment. Such observations provide answers to paradoxes that arise from conceptual frameworks based solely on diffusional spread and reaction of free NO (Lancaster, J. R., (1994); Wood and Garthwaite, *J. Neuropharmacology* 33:1235–1244 (1994)); and has implications that extend to other thiol- and metal-containing (heme) proteins, such as nitric oxide synthase and guanylate cyclase.

The discoveries reported here have direct therapeutic implications. Specifically, concerns over loss of NO-related activity due to inactivation by blood Hb (Lancaster, J. R., (1994)) are obviated by the presence of an RSNO subject to allosteric control. SNO-Hb is free of the adverse hypertensive properties of cell-free Hb preparations that result from NO scavenging at the metal centers. A composition comprising one or more of the various forms of cell-free SNO-Hb (e.g., SNO-Hb[FeII]$O_2$, SNO-Hb[FeIII], SNO-Hb[FeII]CO) can be administered in a pharmaceutically acceptable vehicle to a human or other mammal to act as a blood substitute.

Role of S-Nitrosohemoglobin in Blood Flow Regulation

In the classical allosteric model, Hb exists in two alternative structures, named R (for relaxed, high $O_2$ affinity) and T (for tense, low $O_2$ affinity). The rapid transit time of blood through the capillaries requires that Hb assume the T-structure to efficiently deliver $O_2$ (M. F. Perutz, pp. 127–178 in *Molecular Basis of Blood Diseases*, G. Stammatayanopoulos, Ed. (W.B. Saunders Co., Philadelphia, 1987); Voet, D. and Voet, J. G., pp. 215–235 (John Wiley & Sons Inc., New York, 1995). The switch from R to T in RBCs normally takes place when the second molecule of $O_2$ is liberated. This allosteric transition also controls the reactivity of two highly conserved cysteineβ93 residues that can react with 'NO'. Thiol affinity for NO is high in the R-structure and low in T. This means that the NO group is released from thiols of Hb in low $PO_2$ and explains the arterial-venous (A-V) difference in the S-nitrosohemoglobin (SNO-Hb) level of blood (see Table 2, Example 8). A major function of (S)NO in the vasculature is to regulate blood flow, which is controlled by the resistance arterioles (Guyton, A. C., in *Textbook of Medical Physiology* (W.B. Saunders Co., Philadelphia, 1981) pp. 504–513). It is shown from the Examples herein that (partial) deoxygenation of SNO-Hb in these vessels (Duling, B. and Berne, R. M. *Circulation Research* 27:669 (1970); Popel, A. S., et al., (erratum *Am. J. Physiol.* 26(3) pt. 2). *Am. J. Physiol.* 256:H921 (1989); Swain, D. P. and Pittman, R. N. *Am. J. Physiol.* 256:H247–H255 (1989); Torres, I. et al., *Microvasc. Res.* 51:202–212 (1996); Buerk, D. et al., *Microvasc. Res.* 45:134–148 (1993)) actually promotes $O_2$ delivery by liberating (S)NO. That is, the allosteric transition in Hb functions to release (S)NO in order to increase blood flow.

$O_2$ delivery to tissues is a function of the $O_2$ content of blood and blood flow (Dewhirst, M. W. et al., *Cancer Res.* 54:3333–3336 (1994); Kerger, H. et al., *Am. J. Physiol.* 268:H802–H810 (1995)). Blood oxygen content is largely determined by Hb, which undergoes allosteric transitions in the lung and systemic microvasculature that promote the binding and release of $O_2$ (L. Stryer, in *Biochemistry*, L. Stryer, Ed. (W.H. Freeman & Co., San Francisco, 1981) pp. 43–82; Guyton, A. C. in *Textbook of Medical Physiology* (W.B. Saunders Co., Philadelphia, 1981); Perutz, M. F., pp. 127–178 in *Molecular Basis of Blood Diseases*, G. Stammatayanopoulos, Ed. (W.B. Saunders Co., Philadelphia, 1987); Voet, D. and Voet, J. G. (John Wiley & Sons Inc., New York, 1995) pp. 215–235, pp. 208–215, 224–225, 230–245, 344–355)). Intimate contact between erythrocyte and endothelium is believed to facilitate $O_2$ delivery by minimizing the distance for $O_2$ diffusion into surrounding tissues (Caro, C. G. et al., Oxford University Press, Oxford, 363 (1978)). On the other hand, regional blood flow is regulated by metabolic requirements of the tissue: blood flow is increased by hypoxia and decreased when $O_2$ supply exceeds demand (Guyton, A. C., in *Textbook of Medical Physiology* (W.B. Saunders Co., Philadelphia, 1981) pp. 504–513)). These classical physiological responses are thought to be partly mediated by changes in the level of endothelial-derived NO and its biological equivalents (Park, K. H. et al., *Circ. Res.* 71:992–1001 (1992); Hampl, V. et al., *J. Appl. Physiol.* 75(4):1748–1757 (1993)).

This standard picture is incomplete. First, it has been puzzling that significant $O_2$ exchange occurs in the precapillary resistance vessels (evidenced by the periarteriolar $O_2$ gradient; Duling, B. and Berne, R. M. *Circulation Research* 27:669 (1970); Popel, A. S., et al., (erratum *Am. J. Physiol.* 26(3) pt. 2). *Am. J. Physiol.* 256, H921 (1989); Swain, D. P. and Pittman, R. N. *Am. J. Physiol.* 256:H247–H255 (1989); Torres, I. et al., *Microvasc. Res.,* 51:202–212 (1996); Buerk, D. et al., *Microvasc. Res.,* 45:134–148 (1993)). Why is $O_2$ lost to counter-current venous exchange prior to reaching the tissues? Second, close contact between endothelial surfaces and erythrocytes leads to sequestration of NO by Hb (Stamler, J. S., *Nature* 380:108–111 (1996); Perutz, M. F., *Nature* 380:205–206 (1996)). Decreases in the steady-state levels of NO in terminal arterioles (King, C. E. et al., *J. Appl. Physiol.* 76(3):1166–1171 (1994); Shen, W. et al., *Circulation* 92:3505–3512 (1995); Kobzik, L. et al., *Biochem. Biophys. Res. Comm.* 211(2):375–381 (1995); Persson, M. G., et al., *Br. J. Pharmacol.* 100:463–466 (1990) and capillaries (Mitchell, D., and Tyml, K., *Am. J. Physiol.* 270 *Heart Circ. Physiol.* 39:H1696–H1703 (1996)) contract blood vessels, blunt hypoxic vasodilation and reduce red cell velocity. This line of reasoning leads to the paradox: the red blood cell seems to oppose its own $O_2$ delivery function (note in vivo effects of Hb in FIGS. 10A–10I).

The finding that the $O_2$ gradient in precapillary resistance vessels promotes NO group release from SNO-Hb appears to answer these questions. SNO-Hb compensates for NO scavenging at the heme iron by assuming the T-structure which liberates SNO. Specifically, Cys93 donates the NO group in deoxy structure whereas it cannot do so in the oxy conformation. Accordingly, the $O_2$ gradient determines whether SNO-Hb dilates or constricts blood vessels. Stated another way, SNO-Hb senses the tissue $PO_2$ (i.e., the periarteriolar $O_2$ gradient) and then utilizes the allosteric transition as a means to control arteriolar tone. If the tissue is hypoxic (i.e., the $O_2$ gradient is high), SNO is released to improve blood flow. However, if $O_2$ supply exceeds demand (i.e., the $O_2$ gradient is small), SNO-Hb holds on to the NO group by maintaining the R-structure—with the net effect of reducing blood flow in line with demand. SNO-Hb thereby contributes to the classical physiological responses of hypoxic vasodilation and hyperoxic vasoconstriction.

Based on studies described herein, especially Examples 9–13, the following picture emerges. Partially nitrosylated Hb (Hb[FeII]NO) enters the lung in T-structure (see venous measurements in FIG. 9). There, S-nitrosylation is facilitated by the $O_2$-induced conformational change in Hb. SNO-oxyHb (SNO-Hb[FeII]$O_2$) enters the systemic circulation in R-structure (see arterial levels in FIG. 9). Oxygen losses in precapillary resistance vessels then effect an allosteric transition (from R to T) in Hb which liberates 'NO' to dilate blood vessels (see especially FIGS. 7D and 10A–C). NO released from Hb can be transferred directly to the endothelium, or by way of low mass S-nitrosothiols—such as GSNO—which are exported from RBCs (see especially FIG. 4D and Example 4; see also FIGS. 7C and 11A). Thus, the $O_2$ gradient in arterioles serves to enhance $O_2$ delivery: it promotes an allosteric transition in Hb which releases NO-related activity to improve blood flow.

Further Embodiments

The subject invention relates to a method of loading cells with a nitrosating agent as exemplified for red blood cells as in FIG. 3A, but which can be accomplished in more ways. Suitable conditions for pH and for the temperature of incubation are, for example, a range of pH 7–9, with pH 8 being preferred, and a temperature range of 25 to 37° C. For red blood cells, short incubation times of 1 to 3 minutes are preferred if it is desired to limit the formation of S-nitrosated forms of Hb. However, intracellular concentrations of 1 mM nitrosating agent can be reached.

The nitrosating agent should be a good donor of $NO^+$ and should be able to diffuse through the cell membrane of the target cell type. That is, it is preferably of low molecular weight, in comparison to the molecular weight of S-nitrosoproteins. Examples are S-nitroso-N-acetylcysteine, S-nitrosocysteinylglycine, S-nitrosocysteine, S-nitrosohomocysteine, organic nitrates and nitrites, metal nitrosyl complexes and other related nitrosating agents as defined in "Donors of Nitrogen Oxides" pp. 71–119 In Methods in Nitric Oxide Research (Feelisch, M. and Stamler, J. S., eds.) Wiley, Chichester, U.K. (1996), the contents of which chapter are hereby incorporated by reference in their entirety. Nitrosating agents have differential activities for different reactive groups on metal-containing proteins. A nitrosating agent can be chosen for minimal oxidation of the heme iron of Hb, and maximum activity in nitosylating thiol groups such as found on cysteine. Assay methods are available for detection of nitrosation products, including S-nitrosothiols. See Stamler, et al., U.S. Pat. No. 5,459,076, the contents of which are hereby incorporated by reference in their entirety. See also, for example Keefer, L. K., and Williams, D. L. H., "Detection of Nitric Oxide Via its Derived Nitrosation Products," chapter 35, pp. 509–519 In Methods in Nitric Oxide Research (Feelisch, M. and Stamler, J. S., eds.) John Wiley and Sons, Ltd., Chichester, U.K., 1996; see also Stamler, J. S. and Feelisch, M., "Preparation and Detection of S-Nitrosothiols," chapter 36, pp. 521–539, ibid. Nitrite and nitrate products can be assayed by methods described, for instance, in Schmidt, H. H. H. W. and Kelm, M., "Determination of Nitrite and Nitrate by the Griess Reaction," chapter 33, pp. 491–497, ibid., and in Leone, A. M. and Kelm, M., "Capillary Electrophoretic and Liquid Chromatographic Analysis of Nitrite and Nitrate," chapter 34, pp. 499–507, ibid.

Such low molecular weight nitrosating agents can be used in red blood cells to deliver NO-related activity to tissues in a mammal. Treatment of red blood cells with nitrosating agent further serves to increase the $O_2$ delivery capacity of red blood cells. Such treatment of red blood cells also allows for the scavenging of oxygen free radicals throughout the circulation. It is possible to load red blood cells with S-nitrosothiol, for example, by a process of removing whole blood from a patient's body (as a minimal method of isolating the red blood cells) treating the red blood cells with low molecular weight nitrosating agent, such as by incubating the red blood cells in a solution of low molecular weight nitrosating agent, and then reintroducing the red blood cells into the same patient, thereby allowing the treatment of a number of types of diseases and medical disorders, such as those which are characterized by abnormal $O_2$ metabolism of tissues, oxygen-related toxicity, abnormal vascular tone, abnormal red blood cell adhesion, and/or abnormal $O_2$ delivery by red blood cells. Such diseases can include, but are not limited to, ischemic injury, hypertension, shock, angina, stroke, reperfusion injury, acute lung injury, sickle cell anemia, schistosomiasis and malaria. The use of such "loaded" red blood cells also extends to blood substitute therapy and the preservation of living organs, such as organs for transplantation, for example. In some cases, it can be appropriate to treat a patient with loaded red blood cells originating from a different person.

A particular illustration of the mechanism of the treatment method is presented here by considering sickle cell anemia. Sickle cell patients suffer from frequent vascular occlusive crises which manifest in clinical syndromes such as the acute chest syndrome and hepatic dysfunction. Both endothelial cell dysfunction, resulting in a clotting diathesis as well as dysfunction intrinsic to the red blood cell, are central to disease pathogenesis. At the molecular level, the increased expression of vascular adhesion molecules such as VCAM promote the adhesion of sickled red blood cells containing abnormal hemoglobin. It follows that decreasing cytokine expression on endothelial cells, promoting endothelial function and attenuating red cell sickling, are key therapeutic objectives. However, currently used therapies have been generally unsuccessful.

In this novel method for loading red blood cells with intracellular NO-donor S-nitrosothiols, the effect is to increase oxygen affinity—which in and of itself should attenuate red blood cell sickling—and to endow the red blood cell with vasodilator and antiplatelet activity, which should reverse the vasoocclusive crisis. Moreover, nitric oxide should attenuate the expression of adhesion molecules on endothelial cell surfaces, thus restoring endothelial function.

Herein is described a novel therapeutic approach to the treatment of sickle cell disease which involves loading of red blood cells with S-nitrosothiols or other nitrosating agents. Two examples of therapeutic approaches are given. In the first, the patient's own red blood cells are S-nitrosylated extracorporeally (yielding "loaded" red blood cells) and then given to the patient. The second approach is to directly administer to a patient an agent such as S-nitrosocysteine, which is permeable to red blood cells.

For some diseases or disorders, the administration of NO-loaded red blood cells is especially desirable. Upon a change from the oxygenated to the deoxygenated state, or upon a change in the oxidation state of the heme Fe from the reduced state (FeII) to the oxidized (FeIII) state, NO is released from the thiol groups of hemoglobin, and is rapidly transferred to glutathione to form S-nitrosoglutathione. Red blood cells are known to have a high concentration of glutathione. S-nitrosoglutathione efficiently delivers NO in a biologically active form to tissues.

In another aspect, the invention is a method for the treatment of infection by administering to an infected mammal an agent which causes S-nitrosylation of thiol groups within the cells which are the target of such agent. For example, an S-nitrosothiol to which lymphocytes are highly permeable can be administered to a patient infected with HIV. Such treatment for HIV can also be used extracorporeally, to blood isolated from the patient. In another application, the infection is bacterial, and the S-nitrosothiol to be used as an anti-bacterial agent is one to which the target bacterial cells are highly permeable, as compared to the permeability properties of the host cells. (see, for example, DeGroote, M. A., et al., *Proc. Natl. Acad. Sci. USA* 92:6399–6403 (1995).) Alternatively, nitrosothiols can be used to treat *Plasmodium falciparum* within red blood cells.

Another embodiment of the invention is a method for specifically modifying a protein containing one or more metal atoms so that the protein becomes S-nitrosylated at one or more thiol groups without modifying the metal, as by changing the oxidation state or causing the metal atoms to bind NO. This can be accomplished by the use of a reagent which possesses $NO^+$ character, such as a nitrosothiol (see, for instance, Example 4A), which reacts specifically with thiol groups of a protein in which metal is bound.

For hemoglobin, the nitrosation method does not affect the heme. SNO-oxyHb (SNO-Hb(FeII)$O_2$) can be synthesized from Hb(FeII)$O_2$ with up to 2 SNO groups per tetramer without oxidation of the heme Fe from FeII to FeIII. In contrast, when Hb(FeII)$O_2$ is incubated with excess nitric oxide or nitrite, methemoglobin (HbFe[III]) forms rapidly (Example 1B) and to a significant extent. When Hb[FeII] is incubated with nitric oxide, NO binds rapidly to the heme, forming Hb(FeII)NO to a significant extent (Example 1A).

Although rates of formation of SNO-Hb(FeII)$O_2$ from Hb(FeII)$O_2$ are more rapid (see Example 2A), the corresponding SNO-deoxyHb form can also be made by incubation of S-nitrosoglutathione or S-nitrosocysteine, for example, with Hb(FeII), yielding SNO-Hb(FeII), as in Example 1C.

The effects of the various forms of Hb on vasodilation—constriction, dilation or a neutral effect—depend on three factors: whether 1) the Fe of the heme is oxidized, 2) $O_2$ is bound at the heme (that is, the oxygenation state, dictated by the conformation of the protein as R state or T state), and 3) thiol is present in sufficient concentration to facilitate the transfer of $NO^+$.

The importance of the first factor is shown in FIG. 4A. Hb(FeII)$O_2$ and SNO-Hb[FeII]$O_2$ act as vasoconstrictors, but SNO-Hb[FeIII] (met form, where FeII has been oxidized to FeIII) acts as a vasodilator. FIG. 4A shows that SNO-Hb [FeII]$O_2$, with oxygen bound at the heme, and with a ratio of SNO/Hb=2, acts as a powerful vasoconstrictor.

Figure 2A:
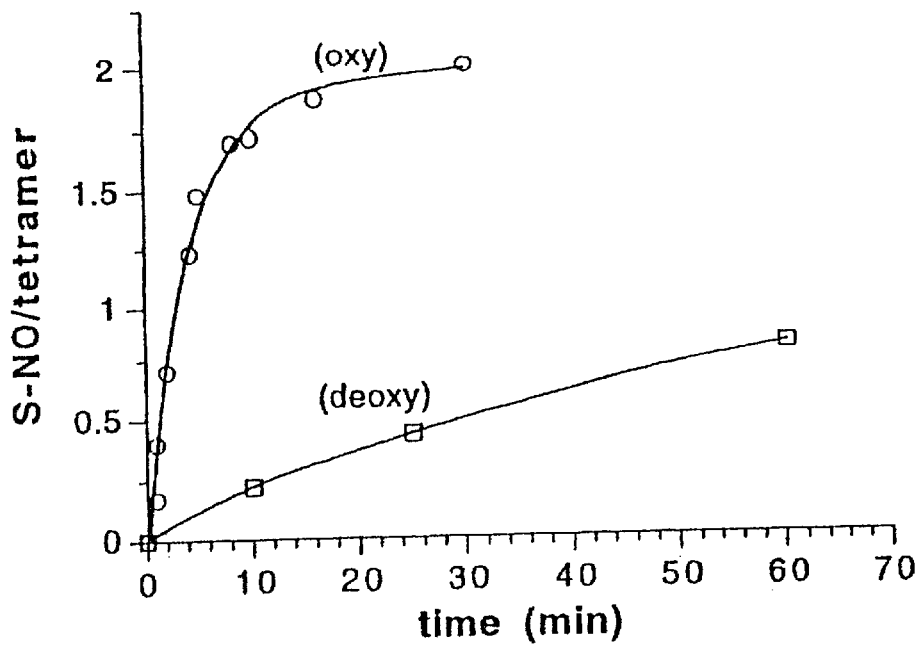
FIG. 2A is a graph showing formation, with time, of SNO-Hb by S-nitrosylation.
Figure 2B:
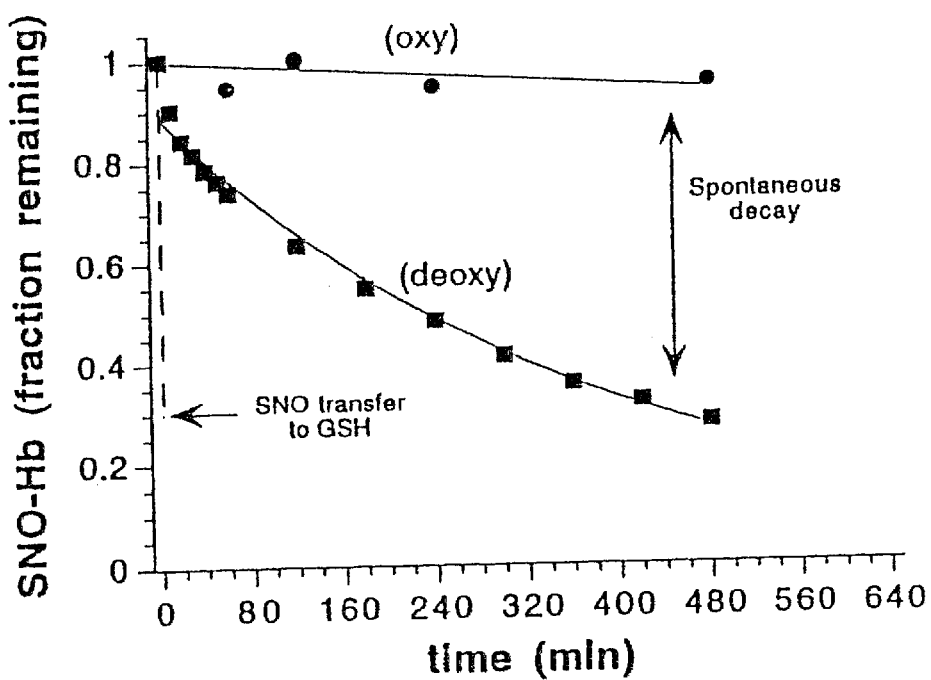
FIG. 2B is a graph showing the decomposition, with time, of oxy and deoxy forms of SNO-Hb.

SNO-Hb(FeII) is also a vasodilator. FIG. 2B illustrates the second factor in demonstrating that rates of RSNO decomposition and transfer are much faster for SNO-Hb in the deoxy state than for SNO-Hb in the oxy state. It can be seen how the $NO^+$-donating properties of SNO-Hb depend on oxygen concentrations. SNO-Hb releases oxygen at sites of low oxygen concentration or under oxidizing conditions. SNO-Hb releases its NO group(s) to cause vasodilation either due to 1) oxidation of the heme Fe to FeIII or 2) loss of the $O_2$ from the heme by deoxygenation. It is shown in FIG. 2B that NO is transferred off SNO-Hb best in the deoxy state. In ischemia, SNO-Hb deoxygenates, rapidly followed by the loss of NO. It can be seen from the data that SNO-metHb having a ratio of 1 SNO/SNO-metHb is a more powerful vasodilator than SNO-oxyHb having a ratio of 2 SNO/SNO-oxyHb. It should be noted that S-nitrosylation of Hb induces the R state (oxy conformation). Thus, it follows that 1 SNO-oxyHb molecule having a ratio of 1 SNO/SNO-oxyHb is less potent than 10 molecules of SNO-oxyHb having a ratio of 0.1 SNO/SNO-oxyHb.

Figure 4B:
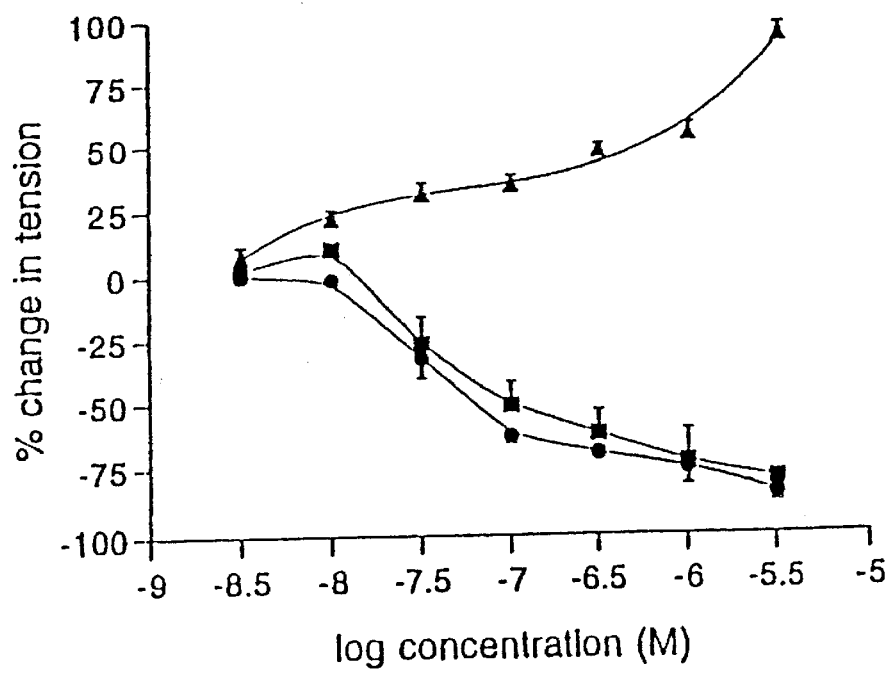
FIG. 4B is a graph of change in tension of a rabbit aortic ring versus concentration of the Hb used in the experiment, wherein glutathione was also added to test the effect as compared to FIG. 4A.
Figure 4C:
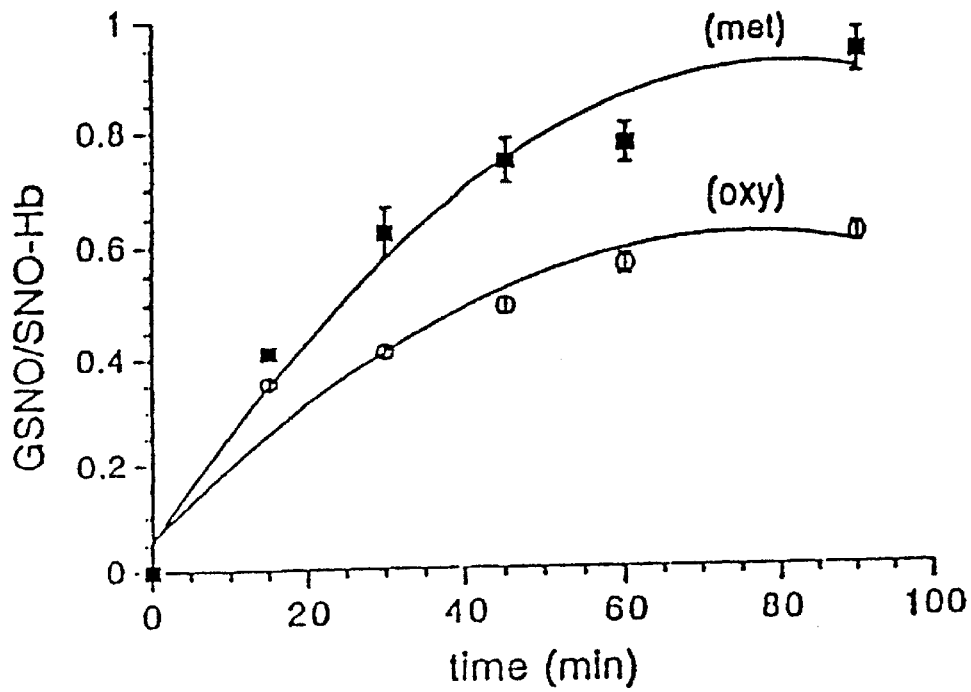
FIG. 4C is a graph of the ratio of S-nitrosoglutathione formed/starting SNO-Hb concentration versus time, showing rates of NO group transfer from oxy and met forms of Hb to glutiathione.

The third factor is illustrated by the results shown in FIG. 4B. These results demonstrate potentiation by thiol of the vasodilator effect of SNO-Hb(FeII)$O_2$ and SNO-Hb(FeIII). Transfer of $NO^+$ from SNO-Hb to low molecular weight nitrosothiols is more efficient when Hb is in the deoxy state compared to the oxy state (FIG. 2B) or in the met state compared to the oxy state (FIG. 4C).

It is thought that NO is released or transferred as $NO^+$ (nitrosyl cation) from SNO-Hb. The SNO groups of SNO-Hb have $NO^+$ character. Transfer of $NO^+$ from SNO-Hb occurs most efficiently to small thiols, such as glutathione, and is most efficient when the heme is oxidized (SNO-metHb) or the SNO-Hb is in the deoxy state.

One embodiment of the invention resulting from these findings is a method of therapy that enhances the transfer of $N^+$ from SNO-Hb to low molecular weight thiols, thereby delivering NO biological activity to tissues, by the coadminstration of low molecular weight thiols, along with a form of SNO-Hb, to a mammal in need of the physiological effects of NO. To further increase the effect of NO release it is preferred that the SNO- forms of metHb or deoxyHb (or an equivalent conformation or spin state) be administered with the thiol (See FIG. 2B, for example.) A mixture of SNO-metHb and SNO-oxyHb, and possibly also thiol, can also be used. The composition and proportion of these components depends on the disease state. For example, to achieve both enhanced $O_2$ delivery and NO delivery, SNO-oxyHb can be used. Where no further delivery of $O_2$ is desirable, as in acute respiratory distress syndrome, for example, the SNO- forms of metHb and deoxyHb are especially preferred. Alternatively, the ratios of SNO/Hb can be regulated to control $O_2$ release.

Figure 5:
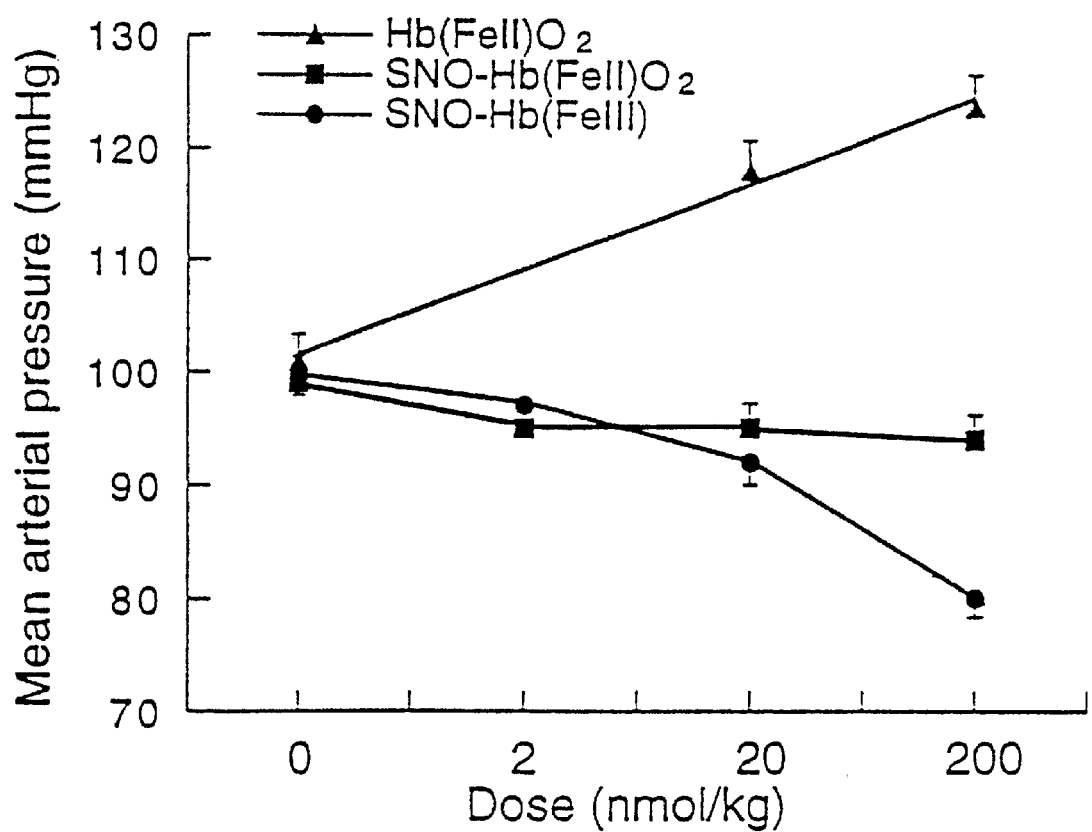
FIG. 5 is a graph showing the mean arterial blood pressure in rats after they received various doses of oxyHb (▲), SNO-oxyHb (■), or SNO-metHb (●).

The vessel ring bioassay data of FIG. 4A agree well with the in vivo data of FIG. 5. The results of the experiments described in Example 5 confirm that Hb(FeII)$O_2$ (oxyHb) causes an increase in blood pressure in vivo, as it did also in vitro. SNO-Hb(FeIII) (SNO-metHb) causes a decrease in blood pressure in vivo as well as in vitro. SNO-Hb(FeII)$O_2$ (SNO-oxyHb) has a negligible effect on blood pressure in vivo in contrast to the increase in tension seen in the corresponding vessel ring bioassay. For SNO-oxyHb the in vivo effect is neutral. This can be explained by the constrictive effect caused by NO becoming bound to the heme being compensated by the release of NO upon deoxygenation. Therefore, SNO-oxyHb can deliver $O_2$ with minimal effect on blood pressure.

With knowledge of the results herein, it is possible to synthesize Hb proteins with predicted NO-releasing properties which will constrict, dilate, or have no effect on blood vessels. An additional option is the choice between making oxygenated or deoxygenated forms to administer for medical conditions in which $O_2$ delivery is desirable, or undesirable, respectively.

It is possible to produce a variety of modified Hbs having specific desired properties of $O_2$ and NO delivery. For example, Hb in the R state (oxyHb) can be converted to the T state (deoxyHb) by a number of known methods. This can be done, for example, by reaction of Hb with inositol hexaphosphate. It is also known to those skilled in the art that Hb in the R state can be made, for example, by treating Hb with carboxypeptidase. Similarly, it is known that metHb can be synthesized using ferricyanide or nitrite.

Producing Hb molecules which are locked in the T state allows the synthesis of RSNO-Hb which remains in a form that is a biologically active donor of NO, rather than a carrier of NO. Hb which is locked in the R state can be used as a substrate for the synthesis of RSNO-Hb which carries a maximum amount of NO per molecule.

Another embodiment of the invention is a blood substitute comprising one or more forms of Hb which have been specifically S-nitrosylated to some extent at one or more thiol groups of the Hb, in order to regulate $O_2$ release and NO release. Conditions to be treated include those in which NO or $O_2$ delivery is desired, those in which NO or $O_2$ utilization is desired, or those in which NO or $O_2$ is in excess. For example, in a medical condition which is characterized by the presence of an excess of oxygen free radicals and excess NO., both the heme of SNO-Hb and NO released by SNO-Hb serve to trap oxygen free radicals. The heme Fe is oxidized in the process of scavenging oxygen free radicals and NO., and NO is released from the oxidized Hb by donation to a thiol, in the form of $RSN^+$ (nontoxic). Inflammation and reperfusion injury, for example, are characterized by excess NO production and an excess of oxygen free radicals. Forms of Hb scavenge oxygen radicals and free NO, converting NO to forms that are not toxic.

A further embodiment of the invention is a method of therapy for a condition that would benefit from the delivery of NO biological activity or $O_2$ or both, based on the administration of a blood substitute comprising a form of SNO-Hb. For example, SNO-Hb is useful to treat myocardial infarction. SNO-Hb has the effect of donating NO, keeping blood vessels open. SNO-Hb deoxygenates at low oxygen tension, delivering oxygen and releasing NO at the same site, thereby causing vasodilation. (See Example 7 and FIGS. 6A–6F.) These effects can be augmented by also administering thiol, either simultaneously with SNO-Hb, or before or after. For the purpose of treating myocardial infarction, for example, a high concentration or dose of SNO-Hb that has a low ratio of SNO/SNO-Hb is appropriate. Alternatively, SNO-metHb can be used for this purpose.

In another aspect, the invention is a method of enhancing NO-donor therapy by coadministering SNO-Hb together with a nitroso-vasodilator (nitroglycerin, for example) which would be otherwise consumed by the conversion of oxyHb to metHb in Hb which has not been S-nitrosylated.

The term hemoglobin or Hb as used herein includes variant forms such as natural or artificial mutant forms differing by the addition, deletion and/or substitution of one or more contiguous or non-contiguous amino acid residues, or modified polypeptides in which one or more residues is modified, and mutants comprising one or more modified amino acid residues. Hb also includes chemically modified forms, as well as genetically altered forms, such as fusion proteins, and truncated forms. It also includes Hbs of all species and variant forms thereof. The biological and/or chemical properties of these variant Hbs may be different from those of hemoglobins which are found naturally occurring in animals.

It will be appreciated that NO (biologically active NO or biological equivalent of NO) exists in biological systems not only as nitric oxide gas, but also in various redox forms and as biologically active adducts of nitric oxide such as S-nitrosothiols, which can include S-nitrosoproteins, S-nitroso-amino acids and other S-nitrosothiols (Stamler, J. S. *Cell* 78:931–936 (1994)).

A blood substitute can be a biologically compatible liquid which performs one or more functions of naturally occurring blood found in a mammal such as oxygen carrying and/or delivery, NO carrying and/or delivery, and the scavenging of free radicals. A blood substitute can also comprise one or more components of such a liquid which, when infused into a mammal, perform one or more functions of naturally occurring blood. Examples of blood substitutes include compositions or preparations of various forms of hemoglobin. Such compositions or preparations can also include other biologically active components, such as a low molecular weight thiol or nitrosothiol.

The compounds and therapeutic preparations of this invention to be used in medical treatment are intended to be used in therapeutic amounts, in suitable compositions, which can be determined by one of skill in the art. Modes of administration are those known in the art which are most suitable to the affected site or system of the medical disorder. A preferred mode of administration of compositions comprising hemoglobins or loaded red blood cells is intravenous.

Suitable pharmaceutical carriers or vehicles can be combined with active ingredients employed in a therapeutic preparation, if necessary. It will be appreciated that the actual amounts of the active components in a specific case will vary according to the specific component being utilized, the particular composition formulated, the mode of administration and the age, weight and condition of the animal or human patient, for example. Dosages for a particular patient can be determined by one of ordinary skill in the art using conventional considerations, (e.g. by means of an appropriate, conventional pharmacological protocol).

The present invention is more specifically illustrated in the following examples, which are not intended to be limiting in any way.

EXEMPLIFICATION

Example 1

Interactions of NO and RSNO With Hb

Figure 1C:
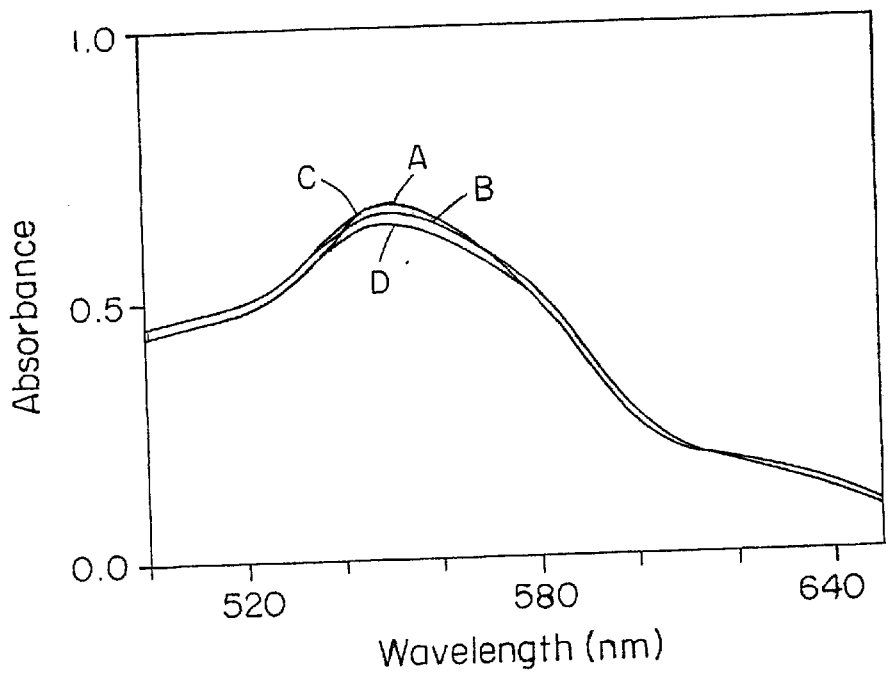
Figure 1D:
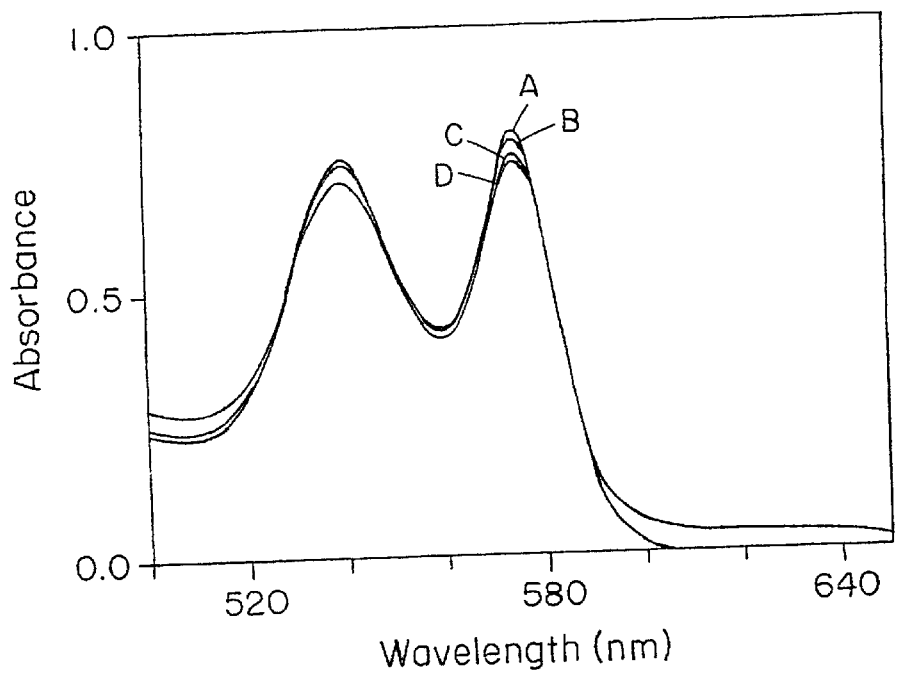

It was observed that naturally occurring N-oxides, such as NO and RSNOs (Gaston, B., et al. (1993; Scharfstein, J. S., et al., *J. Clin. Invest.* 94:1432–1439 (1994); Clancy, R. M., et al., *Proc. Natl. Acad. Sci. USA* 91:3680–3684 (1994)), differed markedly in their reactions with Hb. NO bound very rapidly to deoxyHb (Hb[FeII]), forming relatively stable Hb[FeII]NO complexes (FIG. 1A), and converted oxyHb (Hb[FeII]$O_2$) to methemoglobin (Hb[FeIII]) and nitrate (FIG. 1B), confirming previous reports (Olson, J. S., *Methods in Enzymol.* 76:631–651 (1981); Toothill, C., *Brit. J. Anaesthy.*, 39:405–412 (1967)). In contrast, RSNOs were found to participate in transnitrosation reactions with sulfhydryl groups of Hb, forming S-nitrosohemoglobin (SNO-Hb), and did not react ith the heme centers of either deoxyHb or Hb(FeII)$O_2$ (FIGS. 1C and 1D).

A. Interaction of NO With deoxyHb

Conversion of deoxyHb (Hb[FeII]) to Hb(FeII)NO is observed upon incubation of Hb(FeII) with increasing concentrations of nitric oxide. (See FIG. 1A.) a. Deoxy Hb. b, c, d. Reaction mixtures of NO and Hb(FeII) in ratios of 1:1, 2:1 and 10:1, respectively. The reaction product Hb(FeII)NO formed essentially instantaneously on addition of NO (i.e., within instrument dead time).

B. Interaction of NO With oxyHb

Conversion of oxyHb (Hb[Fe[II]$O_2$) to metHb (HbFe[III]) is observed upon incubation of oxyHb with increasing concentrations of NO. (See FIG. 1B.) a. oxy Hb. b, c, d. Reaction mixtures containing NO and oxyhb in ratios of 1:1, 2:1 and 10:1, respectively. Methemoglobin formation occurred instantaneously on addition of NO (i.e., within instrument dead time).

C. Interaction of S-nitrosothiols With deoxyHb

Conversion of Hb(FeII) to SNO-Hb(FeII) is observed upon incubation of either GSNO (shown) or S-nitrosocysteine (CYSNO) with deoxy Hb. There is little (if any) interaction of RSNO with the heme functionalities of Hb. (See FIG. 1C.) a. deoxyHb. b, c, d. Reaction mixtures of GSNO and Hb(FeII) in ratios of 1:1, 2:1 and 10:1, respectively. Spectra were taken after 60 min of incubation in b, c, and 15 min in d. Further analysis of reaction products revealed the formation of moderate amounts of SNO-Hb in all cases. Yields of SNO-Hb (S-NO/Hb) in b, c, and d at 60 min were 2.5%, 5% and 18.50%, respectively. (See FIG. 1D and FIG. 2A.)

D. Interaction of S-nitrosothiols With oxyHb

Conversion of Hb(FeII)$O_2$ to SNO-Hb(FeII)$O_2$ is observed upon incubation of either GSNO (shown) or CYSNO with oxyHb. There is little (if any) reaction of GSNO (or CYSNO) at the heme centers of Hb(FeII)$O_2$. Specifically, the capacity for $O_2$ binding to heme is unaffected by RSNOs. (See FIG. 1D.) a. oxyHb. b, c, d. Reaction mixtures of GSNO and oxyHb in ratios of 1:1, 2:1, and 10:1, respectively. Spectra were taken after 60 min of incubation in the spectrophotometer. Further analysis of reaction products revealed the formation of SNO-Hb in all cases. Yields of SNO-Hb in spectra b, c and d were 5%, 10% and 50% (S-NO/Hb), respectively. In 5 other determinations, the yield of S-NO/Hb was 0.37±0.06 using GSNO (pH 7.4, 10-fold excess over Hb) and ~2 SNO/tetramer (1.97±0.06 ) using CYSNO (vida infra). These last data are in agreement with reports that human HbA contains 2 titratable SH groups.

Methods

Human HbA$_o$ was purified from red cells as previously described (Kilbourn, R. G., et al., *Biochem. Biophy. Res. Comm.* 199:155–162 (1994)). Nitric oxide solutions were rigorously degassed and purified according to standard procedure (Beckman, J. S., et al., *Methods in Nitric Oxide Research*, Feelisch and Stamler, eds., Wiley Chichester, U.K. (1996)) and saturated solutions were transferred in air tight syringes. Deoxygenation of Hb was achieved by addition of excess dithionite (NO studies) or by reduction of Hb(FeII)$O_2$ through evacuation in Thunberg tubes (RSNO studies; as RSNOs react with dithionite). RSNOs were synthesized as previously described (Gaston, B., et al., (1993); Arnelle and Stamler, *Arch. Biochem. Biophys.* 318:279–285 (1995)). Incubations with HbA$_o$ were made in phosphate buffer, pH 7.4, 0.5 mM EDTA. Quantifications of SNO-Hb were made according to the method of Saville (Gaston, B., et al., (1993); Stamler, J. S., et al., *Proc. Natl. Acad. Sci. USA* 90:444–448 (1992)) after purification of protein with Sephadex G-25 columns. The Saville method, which assays free NO$_x$ in solution, involves a diazotization reaction with sulfanilamide and subsequent coupling with the chromophore N-(naphthyl)ethylenediamine. No low molecular weight S-NO complexes survived this purification and all activity was protein precipitable. The reactions and spectra were carried out using a Perkin Elmer UV/Vis Spectrometer, Lambda 2S.

Example 2

Allosteric Function of $O_2$ in Regulation of Hb S-nitrosylation

Oxygenation of Hb is associated with conformational changes that increase the reactivity of cysβ93 to alkylating reagents (Garel, C., et al., *J. Biochem.*, 123:513–519 (1982); Jocelyn, P. C., *Biochemistry of the SH Group*, Academic Press, London, p. 243 (1972); Craescu, C. T., et al., *J. Biol. Chem.*, 261:14710–14716 (1986)). The physiological importance of this effect has not been explained previously. We observed that rates of S-nitrosylation of Hb were markedly dependent on conformational state. In the the oxy conformation (R state), S-nitrosylation was more rapid than in the deoxy conformation (T state) (FIG. 2A). The rate of S-nitrosylation was accelerated in both conformations by alkaline conditions (i.e., rate at pH 9.2>pH 7.4), which would tend to expose the cysβ93 that is otherwise screened from reaction by the C-terminal histidine 1460. The salt bridge (asp β94 - - - his β146) tying down the histidine residue is loosened at high pH. These data suggest that the increase in thiol reactivity associated with the R state derives, at least in part, from improved NO access rather than a conformation-induced change in pK.

A. Oxygenation Accelerates S-nitrosylation of Hb

Rates of Hb S-nitrosylation by S-nitrosocysteine (CYSNO) are faster in the oxy conformation (Hb[FeII]$O_2$) than in the deoxy state (Hb[FeII]).

Methods

Incubations were performed using 10-fold excess CYSNO over protein (50 μM) in aerated 2% borate, 0.5 mM EDTA (oxyHb), or in a tonometer after rapid $O_2$ evacuation (deoxyHb). At times shown in FIG. 2A, samples were rapidly desalted across G-25 columns (preequilibrated with phosphate buffered saline, 0.5 mM EDTA, pH 7.4) to remove CYSNO, and analyzed for SNO-Hb by the method of Saville (Stamler, J. S., et al., *Proc. Natl. Acad. Sci. USA* 89:444–448 (1992)).

B. Deoxypenation Accelerates Denitrosylation of Hb

Rates of RSNO decomposition (and transfer) are much faster in the deoxy conformation [SNO-Hb(FeII)] than in the oxy state [SNO-Hb(FeII)$O_2$]. The decomposition of SNO-Hb(FeII) is further accelerated by the presence of excess glutathione. Within the dead time of our measurements (~15 sec) a major fraction of SNO-Hb(FeII) was converted to GSNO.

Methods

Hbs in PBS (0.5 mM EDTA, pH 7.4) were incubated in air (oxy) or in a tonometer previously evacuated of $O_2$ (deoxy) SNO-Hb(FeII)$O_2$ decomposition was determined by the method of Saville (Saville, B., *Analyst*, 83:670–672 (1958)). Spontaneous decomposition of SNO-Hb(FeII) was followed spectrophotometrically by formation of Hb(FeII)NO. Transnitrosation reactions with glutathione were performed by addition of 100-fold excess glutathione over protein (50 μM), immediate processing of the reaction mixture under anaerobic conditions followed by rapid TCA precipitation, and analysis of RSNO in the supernatant. Rates of NO group transfer were too rapid to measure accurately by the standard methods used in this study.

Example 3

NO-related Interactions With Cysteine Residues of Hb in Physiological Systems Given that Hb is largely contained within red blood cells, potential mechanisms by which S-nitrosylation of intracellular protein might occur were explored. Incubation of oxygenated rat red blood cells with S-nitrosocysteine resulted in very rapid formation of intracellular SNO-Hb (FeII)$O_2$ (FIG. 3A). Rapid oxidation of Hb was not observed under these conditions. Intraerythrocytic SNO-Hb also formed when red blood cells were treated with S-nitrosohomocysteine or S-nitrosocysteinylglycine, but not with S-nitrosoglutathione (GSNO). Thus, erythrocyte access of RSNOs is thiol group specific. Exposure of oxygenated red blood cells to NO resulted primarily in metHb formation.

Endothelium-Derived Relaxing Factor (EDRF) and Hemoglobin

Hb-mediated inhibition of endothelium-dependent relaxations is commonly used as a marker of NO responses. Inasmuch as reactions with either metal or thiol centers of Hb should lead to attenuated NO/EDRF (endothelium-derived relaxing factor) responses, we attempted to elucidate the molecular basis of inhibition. Hb preparations in which β93 thiol groups had been blocked with N-ethylmaleimide (NEM) or the hemes blocked by cyanmet (FeIIICN)-derivitization were studied in an aortic ring bioassay, and their activities compared with that of native Hb. Both cyanmet-Hb and NEM-Hb caused increases in vessel tone and attenuated acetylcholine (EDRF)-mediated relaxations (FIG. 3B). However, native Hb was significantly more effective than either of the modified Hb preparations (FIG. 3B). Taken in aggregate, these studies suggest that both the thiol and metal groups of Hb contribute to its NO-related activity. To verify formation of an S-nitrosothiol in Hb, we established a bioassay in which 2 cm segments of thoracic aorta were interposed in Tygon tubing, through which 3 cc of Krebs solution containing Hb (4 μM) and ACh (2 μM) were circulated by roller pump (1.5 cc/min×5 min). Analysis of the effluent (Gaston, B., et al., (1993)) revealed the formation of SNO-Hb (20±4 nM) in 5 of 5 experiments.

A. S-nitrosylation of Intraerythrocytic Hb

Incubation of rat erythrocytes with S-nitrosocysteine (equimolar to heme (5 mM); phosphate buffer pH 7.4, 25° C.) leads to rapid formation of intracellular SNO-Hb(FeII)$O_2$. MetHb does not form rapidly. Separation of intracellular RSNOs across G-25 columns reveals that only a small percentage exists as low molecular weight S-nitrosothiol (e.g. GSNO) at most time points. By 60 min, 3 of the 4 available SH groups of Hb are S-nitrosylated (note that rat Hb contains 4 reactive SH groups). (See FIG. 3A.) Inset shows spectra of SNO-Hb isolated from rat erythrocytes and related analyses. Spectrum A is that of SNO-Hb isolated from erythrocytes following G-25 chromatography. Treatment of A with dithionite results in reduction of the S-NO moiety, liberating free NO which is autocaptured by deoxy Hb, forming Hb(FeII)NO (note that dithionite simultaneously deoxygenates Hb) (spectrum C). This spectrum (C) reveals a stoichiometry of ~3 S-NOs per tetramer. The spectrum of Hb(FeII)NO containing 4 NO's per tetramer is shown for comparison (inset, spectrum B).

Methods

At shown intervals, red blood cells were pelleted rapidly by centrifugation, washed three times, lysed in deionized water at 4° C., and the cytosolic fraction subjected to rapid desalting across G-25 columns. Intracellular SNO-Hb was measured by the method of Saville (Gaston, B., et al., (1992); Stamler, J. S., et al., Proc. Natl. Acad. Sci. USA, 89:444–448 (1992)), and confirmed spectroscopically (inset of FIG. 3A) as described above.

B. Molecular Basis of EDRF/Hb Interaction

The effects of native Hb on EDRF responses were compared with Hb preparations in which the thiol or heme centers had been blocked by alkylation or cyanmet derivitization, respectively. All preparations of Hb elicited contractions; however, those of native Hb (in which both SH and metal centers are free for interaction) were most pronounced. (See FIG. 3B.) Likewise, acetylcholine (ACh) mediated relaxations were most effectively inhibited by native Hb. Relaxations were inhibited to lesser degrees by cyanmet Hb (CN-Hb)(in which hemes were blocked from reaction) and NEM-Hb (in which thiol groups were alkylated by N-ethylmaleimide). See Table 1. These data illustrate that both heme and β93SH groups of Hb contribute to reversal of EDRF responses. Direct measurement of SNO-Hb, formed from EDRF under similar conditions, is described in Example 8.

Methods

Descending rabbit thoracic aorta were cut into 3 mm rings and mounted on stirrups attached to force transducers (model FT03, Grass Instruments, Quincy, Mass.) for measurement of isometric tone. The details of this bioassay system have been previously described (Stamler, J. S., et al., Proc. Natl. Acad. Sci. USA 89:444–448 (1992)). Cyanmet Hb was prepared from human HbA according to published protocols (Kilbourn, R. G. et al. Biochem. Biophy. Res. Comm. 199:155–162, (1994)). Alkylation of HbA with N-ethylmaleimide was followed by desalting across G-25 Sephadex to remove excess NEM. Removal of unmodified Hbcysβ93 was achieved by passage through Hg-containing affinity columns. The alkylation of free SH groups was verified using 5,5'-dithio-bis[2-nitrobenzoic acid].

TABLE 1

| ADDITIONS | % INCREASE IN TENSION | % ACh RELAXATION |
|---|---|---|
| Hb (1 μM) | 40.8 ± 2.3 (n = 7) | 31.9 ± 6.9 (n = 7) |
| NEM-Hb (1 μM) | 29.4 ± 1.3** (n = 7) | 60.5 ± 3.9* (n =7) |
| CN-Hb (1 μM) | 12.9 ± 3.0** (n = 6) | 80.7 ± 1.0** † (n = 4) |
| ACh (1 μM) |  | 98.3 ± 0.6 (n = 10) |

*, $P < 0.01$; **, $P < 0.001$, Compared to Hb; †, $P < 0.001$, Compared to ACh

Example 4

Transduction of SNO-Hb Vasoactivity

Arterial red blood cells contain two physiologically important forms of hemoglobin: Hb(FeII)$O_2$ and Hb(FeIII) (Antonini et al. (1971)). Arterial-venous differences in the S-nitrosothiol content of intraerythrocytic Hb suggest that the NO group is released during red cell transit. Such findings raise the possibility of functional consequences, perhaps influenced by the redox state of heme and its occupation by ligand. SNO-Hb(FeII)$O_2$ was found to possess modest NO-like activity when tested in a vascular ring bioassay. Specifically, the contraction elicited by SNO-Hb (FeII)$O_2$ was less than that of native Hb(FeII)$O_2$, indicating that S-nitrosylation partially reverses the contractile effects of Hb (FIG. 4A). By comparison, SNO-Hb(FeIII) was found to be a vasodilator (FIG. 4A). Notably, free NO was devoid of relaxant activity in the presence of Hb(FeII)$O_2$ or Hb(FeIII) (not shown).

Red blood cells contain millimolar concentrations of glutathione. As equilibria among RSNOs are rapidly established through RSNO/thiol exchange (Arnelle and Stamler, J. S., Arch. Biochem. Biophy., 318:279–285 (1995)), the vasoactivity of SNO-Hb was reassessed in the presence of glutathione. FIG. 4B illustrates that glutathione potentiated the vasodilator activity of both SNO-Hb(FeII)$O_2$ and SNO-Hb(FeIII). GSNO formation under these conditions (confirmed chemically and in bioassay experiments) appeared to fully account for this effect. Further kinetic analyses revealed that transnitrosation involving glutathione was more strongly favored in the equilibrium with SNO-Hb (FeIII) than SNO-Hb(FeII)$O_2$ (FIG. 4C). Given the findings of steady-state levels of SNO-Hb in red blood cells (Table 2 and FIG. 3A), these results suggest that 1) the equilibrium between naturally occurring RSNOs and Hb(cysβ93) lies toward SNO-Hb under physiological conditions; 2) that transnitrosation reactions involving SNO-Hb and GSH are likely to occur within red blood cells (the presence of low molecular weight RSNOs in erythrocytes loaded with SNO-Hb has been verified in studies herein); and 3) that oxidation of the metal center of Hb will shift the equilibrium toward GSNO, thereby potentially influencing bioactivity.

Additional mechanisms of NO group release from SNO-Hb were sought. Arterial-venous differences in levels of SNO-Hb raised the possibility that S-NO bond stability may be regulated by the changes in Hb conformation accompanying deoxygenation. To test this possibility, we compared the rates of NO group release from SNO-Hb(FeII)$O_2$ and SNO-Hb(FeIII). Deoxygenation was found to enhance the rate of SNO-Hb decomposition (FIG. 2B). These rates were accelerated greatly by glutathione in a reaction yielding GSNO (FIG. 2B). Our results illustrate that $O_2$-metal interactions influence S-NO affinity, and suggest a new allosteric function for Hb.

Figure 4D:
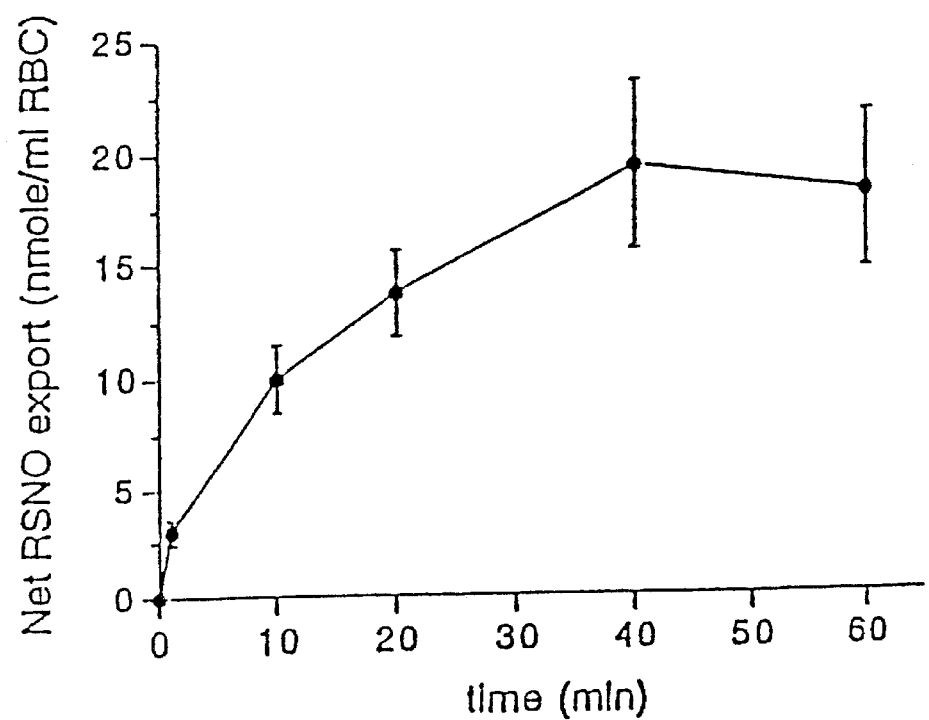
FIG. 4D is a graph of S-nitrosothiols exported from loaded red blood cells over time.

For SNO-Hb to be of physiological importance, it must transduce its NO-related activity across the erythrocyte membrane. We therefore explored this possibility by incubating erythrocytes containing SNO-Hb in physiologic buffer, and measuring the accumulation of extracellular RSNOs over time. FIG. 4D illustrates that red blood cells export low molecular weight (trichloroacetic acid soluble) S-nitrosothiols under these conditions. Importantly, the degree of hemolysis in these experiments was trivial (<0.5%), and correction for lysis did not significantly impact on rates of RSNO release. These results establish that an equilibrium exists between low molecular weight and protein RSNOs within the red cell, and that intracellular location is unlikely to be a limiting factor in the transduction of such NO-related activity to the vessel wall.

A. Concentration-Effect Responses of Different SNO-Hb Preparations

Contractile effects of Hb(FeII)$O_2$(▲) are shown to be partially reversed by S-nitrosylation (SNO-Hb[FeII]$O_2$(■) ;P=0.02 by ANOVA vs Hb(FeII)$O_2$). (See FIG. 4A.) Oxidation of the metal center of SNO-Hb (SNO-Hb[FeIII](●)) converts the protein into a vasodilator (P<0.0001 by ANOVA vs SNO-Hb[FeII]$O_2$), with potency comparable to that of other S-nitrosoproteins (Stamler, J. S., et al., Proc. Natl. Acad. Sci. USA 89:444–448 (1992)). The contractile properties of Hb(FeIII) are shown for comparison (□); n=6–17 for each data point.

Methods

Details of the vessel ring bioassay have been published (Stamler, J. S., et al., Proc. Natl. Acad. Sci. USA 89:444–448 (1992)). SNO-Hb(FeII)$O_2$ preparations were synthesized with 10-fold excess S-nitrosocysteine (CYSNO) over Hb(FeII)$O_2$ protein (2% borate, 0.5 mM EDTA, ~15 min incubation), after which desalting was performed across Sephadex G-25 columns. CYSNO was synthesized in 0.5 N HCl, 0.5 mM EDTA and then neutralized (1:1) in 1 M phosphate buffer containing 0.5 mM EDTA. SNO-Hb(FeIII) preparations followed a similar protocol, but used Hb(FeIII) as starting material. The latter was synthesized by treatment of Hb(FeII)$O_2$ with excess ferricyanide, followed by desalting across G-25 columns. SNO-Hb concentrations were verified spectroscopically and the S-nitrosothiol content was determined by the method of Saville (Stamler, J. S., et al., Proc. Nat. Acad. Sci. USA 89:444–448 (1992)). The S-NO/ tetramer stoichiometry for both SNO-Hb preparations was ~2. Oxidation of the heme was undetectable by uv-spectrophotometric methods.

B. Potentiation of SNO-Hb Effects by Glutathione

Addition of glutathione (100 $\mu$M) to bioassay chambers potentiates the dose-response to both SNO-Hb(FeII)$O_2$(■) and SNO-Hb(FeIII)(●) (See FIG. 4B. n=6–12; p<0.0001 for both by ANOVA, compared with the respective tracings in FIG. 4A). Glutathione had a transient affect on baseline tone in some experiments, and did not significantly influence the response to Hb(FeII)$O_2$ (▲).

C. Transnitrosation Between SNO-Hb and Glutathione

Rates of NO group transfer from SNO-Hb (100 $\mu$M) to glutathione (10 mM) are displayed for SNO-Hb(FeII)$O_2$ (OXY) and SNO-Hb(FeIII) (met) (n=5). Data are presented as the amount of GSNO formed relative to the starting SNO-Hb concentration. The transfer is more rapid for SNO-Hb(FeIII) than SNO-Hb(FeII)$O_2$ (p<0.002 by ANOVA), suggesting that the GSNO/SNO-Hb equilibrium is shifted toward GSNO by formation of met Hb.

Methods

Thiol/SNO-Hb exchange, forming GSNO, was verified chemically (Stamler, J. S., et al., Proc. Natl Acad. Sci. USA 89:444–448 (1992)) following trichloroacetic acid precipitation (n=5). These results were verified in separate experiments by measuring the residual SNO-Hb concentration, following separation of reaction mixtures accross G-25 columns.

D. Export of S-nitrosothiols by Red Blood Cells

Human red blood cells containing SNO-Hb are shown to export low molecular weight RSNOs over time. Hemolysis, which ranged from 0–<0.5% over one hour and did not correlate with rates of RSNO release, could account for only a trivial fraction of the measured extracellular RSNO.

Methods

Packed human red blood cells were obtained by centrifugation, washed, and resuspended in phosphate buffered saline containing 5 mM SNOCYS (0.5 mM EDTA, pH 7.4) for one hour. This results in a red cell preparation containing SNO-Hb (FeII$O_2$/FeIII mixture) with a stoichiometry of 0.5 S-NO/tetramer. The red blood cells were then washed repeatedly to remove residual CYSNO (verified), and incubated in Krebs' solution (1:4). The accumulation of extracellular RSNO was measured over time by the method of Saville (Saville, B., Analyst, 83:670–672 (1958)). Hemolysis was determined by spectral analysis of red blood cell supernatants following centrifugation.

Example 5

SNO-Hb Bioactivity In Vivo

Systemic administration of cell-free Hb results in hypertensive responses which have been attributed to NO scavenging by the heme (Vogel, W. M., et al., Am. J. Physiol. 251:H413–H420 (1986); Olsen, S. B., et al., Circulation 93:329–332 (1996)). To determine if SNO-Hb is free of this adverse affect, and to explore if in vitro mechanisms of NO release extend to the in vivo circumstance, we compared responses to Hb and SNO-Hb infused as a bolus into the femoral vein of anesthetized rats. As illustrated in FIG. 5, Hb(FeII)O$_2$ (200 nmol/kg) caused an increase in mean arterial pressure of 20±3 mm Hg (n=4; P<0.05). In contrast, SNO-Hb(FeII)O$_2$ did not exhibit hypertensive effects and SNO-Hb(FeIII) elicited hypotensive responses (FIG. 5). Thus, the profiles of these compounds in vivo closely resemble those seen in vitro (FIG. 4A). Moreover, to demonstrate that the physiological responses of red cells are comparable to those of cell-free Hb preparations, erythrocytes containing SNO-Hb were injected into the femoral vein of rats pretreated with L-NMMA (50 mg/kg) to deplete endogenous RSNOs. At levels of SNO-Hb comparable to those found in the normal rat (0.1–0.5 $\mu$M), SNO-Hb containing red blood cells elicited hypotensive responses (8±1 mm Hg; mean±SEM; n=9), whereas native (SNO-Hb depleted) red blood cells did not (P=0.001). These changes in mean blood pressure of ~10% are on the order of those that differentiate normotension from hypertension in man, and in the therapeutic range of some antihypertensive regimens. The effects of both Hb and SNO-Hb—whether cell-free or contained within red cells—were transient, suggesting that S-nitrosylation of Hb and metabolism of SNO-Hb is occurring in vivo, with consequent: restoration of blood pressure. The bioactivity of SNO-Hb in blood, where S-NO/heme stoichiometries approach 1:50,000, is a dramatic illustration of the resistence of this NO-related activity to Hb(Fe) inactivation.

In vivo Effects of Cell-Free Hb and SNO-Hbs

Administration of 2–200 nmol/kg Hb(FeII)O$_2$ (as a bolus) into the femoral vein of a Sprague-Dawley rat is shown to increase mean arterial pressure in a dose-dependent manner. At 200 nmol/kg, mean arterial pressure increased by 25 mm Hg (20±3 mm Hg; n=4; P<0.05). Elevations in blood pressure reversed within 10–15 min. SNO-Hb(FeII)O$_2$ infusions (over the same dose range) are shown to ameliorate Hb(FeII)O$_2$-induced hypertension without causing overt changes in blood pressure. A similar response was seen at higher doses. By comparison, SNO-Hb(FeIII) infusions caused a significant fall in mean arterial pressure (pre 108±4 mm Hg; post 74±6 mm Hg, n=5; P<0.05) at the highest dose (200 nmol/kg). Hypotensive responses tended to be transient with blood pressure normalizing over 10 minutes. A fall in blood pressure was also seen with injection of erythrocytes containing SNO-Hb.

Methods

Rats were anesthetized by intraperitoneal injection of pentobarbital and the femoral arteries and veins accessed by local cut down. The artery was then cannulated and the blood pressure monitored continuously using a Viggo Spectramed pressure transducer attached to a Gould recorder. An IBM PC (DATA Q Codas) was used for data acquisition.

Example 6

Loading of Red Blood Cells With S-Nitrosothiols

Incubation of rat erythrocytes with S-nitrosocysteine (equimolar to heme (5 mM); phosphate buffer pH 7.4, 25° C.) leads to rapid formation of intracellular S-nitrosothiols. MetHb does not form rapidly. Separation of cell content across G-25 columns establishes the formation of intraerythrocytic low molecular weight S-nitrosothiol, e.g. S-nitrosoglutathione (GSNO). By 2 min., one can achieve as much as millimolar GSNO.

Method for Assay of RSNO

S-nitrosocysteine (5 mM) treated red blood cells are pelleted rapidly by centrifugation, washed three times, lysed in deionized water at 4° C., and the cytosolic fraction subjected to rapid desalting across G-25 columns. Intracellular RSNO is measured by the method of Saville and can be confirmed spectroscopically.

Effects on Blood Pressure From Loaded Red Blood Cells

Red blood cells treated with S-nitroscysteine (to produce SNO-RBCs) and introduced into the femoral vein of a Sprague-Dawley rat decreased mean arterial pressure in a dose-dependent manner. For red blood cells in which SNO-Hb was assayed at 0.3 $\mu$M (the endogenous in vivo SNO-Hb concentration), arterial pressure decreased by 8±1 mm Hg (mean+SEM for 9 experiments; p<0.001 compared to untreated red blood cell controls). For red blood cells in which SNO-Hb was assayed at 0.5 $\mu$M, arterial pressure decreased by 10 mm Hg. For red blood cells in which SNO-Hb was assayed at 0.1 $\mu$M (a sub-endogenous SNO-Hb concentration), arterial pressure decreased by 6 mm Hg. The administration of untreated red blood cells caused no effect or a slight increase in arterial blood pressure. Administration of L-monomethyl-L-arginine (L-NMMA; 50 mg/kg) caused an increase in blood pressure of about 20 mm Hg. Changes in blood pressure from a bolus administration of loaded red blood cells lasted 15–20 minutes.

Further Methods

Rats were anesthetized by intraperitoneal injection of pentobarbital and the femoral arteries and veins accessed by local cut down. The artery was then cannulated and the blood pressure monitored continuously using a Viggo Spectramed pressure transducer attached to a Gould recorder. An IBM PC (DATA Q Codas) was used for data acquisition.

Example 7

Effects of SNO-Hb on Coronary Vasodilation, Coronary Flow and Blood Pressure

SNO-Hb was synthesized as described in Example 4A. Completion of the reaction was determined as described in Example 4A. Twenty-four healthy mongrel dogs (25–30 kg) were anesthetized with intravenous thiamylal sodium (60–80 mg/kg) and subjected to left thoracotomy in the fourth intercostal space. The left circumflex coronary artery distal to the left aural appendage was minimally dissected. A pair of 7-MHz piezoelectric crystals (1.5×2.5 mm, 15–20 mg) was attached to a Dacron backing and sutured to the adventitia on opposite surfaces of the dissected vessel segment with 6-0 prolene. Oscilloscope monitoring and on-line sonomicrometry (sonomicrometer 120-2, Triton Technology, San Diego, Calif.) were used to ensure proper crystal position. A pulse Doppler flow probe (10 MHz, cuff type) was implanted distal to the crystals. An inflatable balloon occluder was also placed distal to the flow probe. All branches of the circumflex artery between the crystals and the occluder were ligated. Heparin sodium-filled polyvinyl catheters were inserted into the left ventricular cavity via the apex, into the left atrium via the aural appendage, and into the ascending aorta via the left internal thoracic artery. The catheters, tubing, and wires were tunnelled to a subcutaneous pouch at the base of the neck.

After a 10 to 15 day recovery period, the catheters and wires were exteriorized under general anesthesia, and 2–3 days later, each dog was given a bolus injection of SNO-Hb (0.4 mg) to evaluate vascular response. Two dogs that demonstrated <5% dilation of epicardial coronary vessels were excluded from subsequent studies, and two were excluded because of other technical reasons.

Dogs were trained and studied while loosely restrained and lying awake in the lateral recumbent position. The laboratory was kept dimly illuminated and quiet. Aortic pressure, left ventricular end-diastolic pressure dP/dt external coronary diameter and coronary flow were monitored continuously. In 10 dogs, 0.1 ml of SNO-Hb solution, 50 nM/kg, was injected via the left aural catheter. To verify potential effects of solvent on vasculature, 0.1 ml injections of 30% ethanol in distilled water were given as vehicle control. Between injections, phasic coronary blood flow and coronary artery diameter were allowed to return to preinjection levels (minimum 15 minutes). Allowing a 15 minute period between injections resulted in no modification of repeated dose injections. To assess the direct and potential flow mediated indirect vasodilation effects of SNO-Hb on the conductance vessels, the dose was repeated in 6 of 10 dogs with partial inflation of the adjustable occluder to maintain coronary blood flow at or slightly below preinjection levels. The response to acetylcholine chloride (Sigma Chemical) was assessed in another group of 10 dogs following a similar protocol to that used for SNO-Hb.

Epicardial coronary diameter, coronary blood flow, heart rate, and aortic and left ventricular end-diagnostic pressures were compared before and after each SNO-Hb injection. The maximum changes in coronary dimension and blood flow were expressed as a function of increasing doses of SNO-Hb. The response of coronary dimension to increasing doses followed a characteristic sigmoid dose-response curve that could be described by the following equation $$\text{Effect} = \frac{\text{maximal effect} \times \text{dose}}{K_D + \text{dose}}$$

where $K_D$ is the drug-receptor complex dissociation constant and is the dose at which 50% of the maximum response ($EC_{50}$) is achieved. In each animal, a nonlinear least-squares regression ($r^2 > 0.90$) was performed on the dose-response data. The regression was constrained to the above equation. From the regression, values for maximum response and $K_D$ were obtained for each individual animal. The mean of these values was then calculated to obtain an average $K_D$ and maximum response for the study group. These values were used to generate a mean curve, which was plotted with he mean dose-response values. (See FIGS. 6A–6F.)

Example 8

Endogenous Levels of S-nitrosohemoglobin and Nitrosyl(FeII)-Hemoglobin in Blood

To determine if SNO-Hb is naturally occuring in the blood, and if so, its relationship to the $O_2$ transport capacity and nitrosylated-heme content of red cells, we developed an analytical approach to assay the S-nitrosothiol and nitrosyl-heme content of erythrocytes (Table 2). Arterial blood was obtained from the left ventricle of anesthetized rats by direct puncture and venous blood was obtained from the jugular vein and inferior vena cava. Hb was then purified from red cells and assayed for RSNO and (FeII)NO content. Arterial blood contained significant levels of SNO-Hb, whereas levels were virtually undetectable in venous blood (Table 2). Measurements made 45 minutes after infusion of the NO synthase inhibitor $N^\omega$-monomethyl-L-arginine (L-NMMA) (50 mg/kg), showed a depletion of SNO-Hb as well as total Hb-NO (82 and 50±18%, respectively; n=3–5; p<0.05). These data establish the endogenous origin of SNO-Hb, although some environmental contribution is not excluded.

The arterial-venous distribution seen for SNO-Hb was reversed in the case of Hb(FeII)NO, which was detected in higher concentrations in partially deoxygenated (venous) erythrocytes (Table 2). Accordingly, the proportion of nitrosylated protein thiol and heme appears to depend on the oxygenation state of the blood. Consistent with these findings, Wennmalm and coworkers have shown that Hb(FeII)NO forms mainly in venous (partially deoxygenated) blood (Wennmalm, A., et al., *Br. J. Pharmacol.*, 106(3):507–508 (1992)). However, levels of Hb(FeII)NO in vivo are typically too low to be detected (by EPR) and SNO-Hb is EPR-silent (i.e. it is not paramagnetic). Thus, photolysis-chemiluminesence represents an important technological advance, as it is the first methodology capable of making quantitative and functional assessments of NO binding to Hb under normal physiological conditions.

TABLE 2

Endogenous Levels of S-Nitrosohemoglobin and Nitrosyl(FeII)-Hemoglobin in Blood

| Site | SNO-Hb (nM) | Hb(FeI)NO (nm) |
|---|---|---|
| Arterial | 311 ± 55* | 536 ± 99 † |
| Venous | 32 ± 14 | 894 ± 126 |

*P < 0.05 vs venous; † P < 0.05 for paired samples vs venous

Methods

Blood was obtained from the left ventricle (arterial) and jugular vein (venous) of anesthetized Sprague-Dawley rats. Comparable venous values were obtained in blood from the inferior vena cava. Red blood cells were isolated by centrifugation at 800 g, washed three times in phosphate buffered saline at 4° C., lysed by the addition of 4-fold excess volume of deionized water containing 0.5 mM EDTA, and desalted rapidly across G-25 columns according to the method of Penefsky at 4° C. In 24 rats, Hb samples were divided in two aliquots which were then treated or not treated with 10-fold excess $HgCl_2$ over protein concentration as measured by the method of Bradford. Determinations of SNO-Hb and Hb(FeII)NO were made by photolysis-chemiluminescence as described below. In 12 additional rats, further verification of the presence of SNO-Hb was made by assaying for nitrite after $HgCl_2$ treatment. Specifically, samples (with and without $HgCl_2$) were separated across Amicon-3 (Centricon filters, m.w. cut off 3,000) at 4° C. for 1 h, and the low molecular weight fractions collected in airtight syringes containing 1 μM glutathione in 0.5 N HCl. Under these conditions, any nitrite present was converted to S-nitrosoglutathione, which was then measured by photolysis-chemiluminescence (detection limit ~1 nM). SNO-Hb was present in all arterial samples, and levels determined by this method (286±33 nM) were virtually identical to and not statistically different from those shown in Table 2. In venous blood, SNO-Hb was undetectable (0.00±25 nM); levels were not statistically different from those given above.

Method for Assay of S-nitrosohemoglobin

A highly sensitive photolysis-chemiluminescence methodology was employed. A somewhat similar assay has been used for measuring RSNOs (S-nitrosothiols) in biological systems (Gaston, B., et al., (1993); Stamler, J. S., et al., *Proc. Natl. Acad. Sci. USA* 89:7674–7677 (1992)). The method involves photolytic liberation of NO from the thiol, which is then detected in a chemiluminesence spectrometer by reaction with ozone. The same principle of operation can be used to cleave (and measure) NO from nitrosyl-metal compounds (Antonini, E. Brunori, M. In *Hemoglobin and Myoglobin in*

*Their Reactions with Ligands,* American Elsevier Publishing Co., Inc., New York, pp. 29–31 (1971)). With adjustment of flow rates in the photolysis cell, complete photolysis of the NO ligand of Hb(FeII)NO could be achieved. Standard curves derived from synthetic preparations of SNO-Hb, Hb(FeII)NO, and S-nitrosoglutathione were linear (R>0.99), virtually superimposable, and revealing of sensitivity limits of approximately 1 nM. Two analytical criteria were then found to reliably distinguish SNO-Hb from Hb(FeII)NO: 1) signals from SNO-Hb were eliminated by pretreatment of samples with 10-fold excess $HgCl_2$, while Hb(FeII)NO was resistant to mercury challenge; and 2) treatment of SNO-Hb with $HgCl_2$ produced nitrite (by standard Griess reactions) in quantitative yields, whereas similar treatment of Hb(FeII) NO did not. UV/VIS spectroscopy confirmed that NO remained attached to heme in the presence of excess $HgCl_2$.

Example 9

Oxygen-Dependent Vasoactivity of S-Nitrosohemoglobin: Contraction of Blood Vessels in R-Structure and Dilation in T-Structure The details of this bioassay system have been published (Osborne, J. A., et al., *J. Clin. Invest.* 83:465–473 (1989)). In brief, New Zealand White female rabbits weighing 3–4 kg were anesthetized with sodium pentobarbital (30 mg/kg). Descending thoracic aorta were isolated, the vessels were cleaned of adherent tissue, and the endothelium was removed by gentle rubbing with a cotton-tipped applicator inserted into the lumen. The vessels were cut into 5-mm rings and mounted on stirrups connected to transducers (model TO3C, Grass Instruments, Quincy, Mass.) by which changes in isometric tension were recorded. Vessel rings were suspended in 7 ml of oxygenated Kreb's buffer (pH 7.5) at 37° C. and sustained contractions were induced with 1 $\mu$M norepinephrine.

Best attempts were made to achieve equivalent baseline tone across the range of oxygen concentrations; i.e., hypoxic vessels were contracted with excess phenylephrine. Oxygen tension was measured continuously using $O_2$ microelectrodes (Model 733 Mini; Diamond General Co., MI) (Young, W., *Stroke,* 11:552–564 (1980); Heiss, W. D. and Traupett, H., *Stroke,* 12:161–167 (1981); Dewhirst, M. W. et al., *Cancer Res.,* 54:3333–3336 (1994); Kerger, H. et al., *Am. J. Physiol.,* 268:H802–H810 (1995)). Less than 1% $O_2$ corresponds to 6–7 torr. Hypoxic vessels were contracted with excess phenylephrine to maintain tone. SNO-Hb[FeII] $O_2$ (SNO-oxyHb) preparations were synthesized and quantified as in Example 14; GSNO was prepared and assayed as described in Stamler, J. S. and Feelisch, M., "Preparation and Detection of S-Nitrosothiols," pp. 521–539 in *Methods In Nitric Oxide Research* (M. Feelisch and J. S. Stamler, eds.), John Wiley & Sons Ltd., 1996.

Hemoglobin is mainly in the R (oxy)-structure in both 95% $O_2$ or 21% $O_2$ (room air) (M. F. Perutz, pp. 127–178 in *Molecular Basis of Blood Diseases,* G. Stammatayanopoulos, Ed. (W.B. Saunders Co., Philadelphia, 1987); Voet, D. and Voet, J. G. (John Wiley & Sons Inc., New York, 1995) pp. 215–235). Hb and SNO-Hb both contract blood vessels over this range of $O_2$ concentrations. That is, their hemes sequester NO from the endothelium. The functional effects of these hemoproteins in bioassays are not readily distinguished (FIG. 7A). Concentration-effect responses of SNO-Hb are virtually identical to those of native Hb in 95% $O_2$—i.e., in R-structure (curves are not different by ANOVA; n=12 for each data point). Comparable contractile effects were seen with up to 50 $\mu$M SNO-oxyHb/oxyHb—i.e., at doses where the responses had plateaued. Similar concentration-effect responses were observed in 21% $O_2$, under which condition Hb/SNO-Hb is ~99% saturated (data not shown).

On the other hand, hypoxia (<1% $O_2$ [~6 mm Hg] simulating tissue $PO_2$) which promotes the T-structure (M. F. Perutz, pp. 127–178 in *Molecular Basis of Blood Diseases,* G. Stammatayanopoulos, Ed. (W.B. Saunders Co., Philadelphia, 1987); Voet, D. and Voet, J. G. (John Wiley & Sons Inc., New York, 1995) pp. 215–235), differentiates Hb and SNO-Hb activities: Hb strongly contracts blood vessels in T structure whereas SNO-Hb does not (FIG. 7B). Concentration-effect responses of SNO-Hb and Hb are significantly different <1% $O_2$ (~6 torr), i.e. in T-structure. Native deoxyHb is a powerful contractile agent whereas SNO-deoxyHb has a modest effect on baseline tone. (In most experiments SNO-Hb caused a small degree of contraction at lower doses and initiated relaxations at the highest dose; in some experiments (see FIG. 8C) it caused dose-dependent relaxations.) n=13 for each data point; *P<0.05; ***P<0.001 by ANOVA.

SNO-Hb relaxations are enhanced by glutathione through formation of S-nitrosoglutathione (GSNO) (FIG. 7C). The potentiation of SNO-Hb vasorelaxation by glutathione is inversely related to the $PO_2$ (FIG. 7C) because NO group transfer from SNO-Hb is promoted in the T-structure. Specifically, transnitrosation of glutathione by SNO-Hb— forming the vasodilator GSNO—is accelerated in T-structure (<1% $O_2$). Addition of 10 $\mu$M glutathione to bioassay chambers potentiates the vasorelaxant response of SNO-Hb. The potentiation is greatest under hypoxic conditions; i.e., the curve for <1% $O_2$ shows a statistically significant difference from both the 95% and 21% $O_2$ curves (P<0.001), which are not different from one another by ANOVA (n=6 for all data points). High concentrations of glutathione (100 $\mu$M–1 mM) further potentiate SNO-Hb relaxations, such that the response is virtually identical to that seen in the presence of GSNO in FIG. 7D. Glutathione at 10 $\mu$M has no effect on native Hb contractions.

In contrast, the vasorelaxant effects of S-nitrosoglutathione are largely independent of $PO_2$ (FIG. 7D) and unmodified by superoxide dismutase (not shown). Concentration-effect responses of S-nitrosoglutathione (GSNO) are largely independent of $PO_2$ in the physiological range (n=6 at each data point). Results are consistent with known resistance of GSNO to $O_2/O_2^-$ inactivation (Gaston, B. et al., *Proc. Natl. Acad. Sci. USA,* 90:10957–10961 (1993)). Thus, in T-structure, relaxation by SNO overwhelms the contraction caused by NO scavenging at the heme, whereas the opposite is true in R-structure.

Example 10

Bioactivity of Intraerythrocytic S-Nitrosohemoglobin (SNO-RBCs)

Contractile effects of RBCs are reversed by intracellular SNO-Hb in low but not high $PO_2$—i.e., under conditions that promote the T-structure. Low and high dose effects of SNO-RBCs are shown in FIGS. 8A and 8B, respectively.

Preparation of vessel rings and methods of bioassay are described in Example 9. SNO-oxyHb was synthesized and quantified as described in Example 14. Red blood cells containing SNO-Hb (SNO-RBCs) were synthesized by treatment with tenfold excess S-nitrosocysteine over hemoglobin for 5–10 min. Under this condition, red blood cells are bright red and contain SNO-oxyHb; metHb was not detectable in these experiments.

Red blood cells containing SNO-Hb (SNO-RBCs) function in vessel ring bioassays like cell-free SNO-Hb. In particular, low concentrations of SNO-RBCs (~0.1 $\mu$M SNO-Hb) elicited modest contractile effects in 95% $O_2$, but not under hypoxia (FIG. 8A). In 95% $O_2$, both SNO-RBCs (~0.1 $\mu$M SNO-Hb[FeII]$O_2$) and native RBCs produced modest contractile effects that were not readily distinguished. The contractions by RBCs tended to be greater under hypoxic conditions (<1% $O_2$), whereas those of SNO-RBCs were reversed (slight relaxant effects were seen). These $O_2$-dependent responses of SNO-RBCs closely resemble those of cell-free preparations. Hemolysis was minor and could not account for the observed effects.

At higher concentrations, SNO-RBCs produced small transient relaxations in 95% $O_2$ and larger sustained relaxations under hypoxia (FIG. 8B), much like cell-free SNO-Hb in the presence of glutathione. For example, SNO-RBCs (~1 $\mu$M SNO-Hb[FeII])$_2$) caused 32.5±1.26 relaxation that lasted 14.5±0.7 min. in 95% $O_2$ versus 61±10% relaxation that lasted 23± min. in <1% $O_2$ (n=3–4; P<0.05) In contrast, RBCs containing no SNO-Hb produced small contractions (less than those of cell-free Hb) that are potentiated by hypoxia (13±2.0% in 95% $O_2$ vs. 25±5% in <1% $O_2$; P<0.05). Hemolysis in these experiments was minor and could not account for the extent of relaxation by SNO-RBCs.

In 95% $O_2$, SNO-RBCs (~1/$\mu$M SNO-Hb[FeII]$O_2$) produced relaxations of aortic rings, whereas native RBCs produced slight contractions. Both effects were more prominent at low $PO_2$. That is, relaxations and contractions of intraerythrocytic SNO-Hb and Hb, respectively, were greater and longer-lived in <1% $O_2$ than in 95% $O_2$. The $O_2$-dependent responses of SNO-RBCs mimicked those of cell-free SNO-Hb in the presence of glutathione. Hemolysis in these experiments was minor and could not account for the extent of relaxation by SNO-RBCs.

The normal response of systemic arteries to hypoxia is dilation and contraction to high $PO_2$. The responses of vessel rings to changes in $PO_2$ in the presence of SNO-Hb and Hb were tested (FIG. 8C). Vessel rings were contracted with phenylephrine under hypoxic conditions (6–7 torr) and then exposed to either 1 $\mu$M Hb or SNO-Hb. Hb produced progressive increases in vessel tone, while SNO-Hb caused relaxations. Introduction of 95% $O_2$ led to rapid contractions in both cases. Thus, structural changes in SNO-Hb effected by $PO_2$ are rapidly translated into contractions or relaxations, whereas Hb contracts vessels in both R- and T-structures. Thus, Hb opposes the physiological response and SNO-Hb promotes it (FIG. 8C). Direct effects of $O_2$ on smooth muscle operate in concert with SNO-Hb to regulate vessel tone.

Example 11

Influence of $O_2$ Tension on Endogenous Levels of S-Nitrosohemoglobin (SNO/Hb) and Nitrosyl Hemoglobin (FeNO/Hb)

Allosteric control of SNO-Hb by $O_2$ was assessed in vivo by perturbation of the periarteriolar oxygen gradient. In animals breathing room air (21% $O_2$), the precapillary resistance vessels (100–10 $\mu$m) are exposed to $PO_2$s as low as 10–20 torr (Duling, B. and Berne, R. M. *Circulation Research*, 27:669 (1970); Popel, A. S., et al., (erratum *Am. J. Physiol.* 26(3) pt. 2) *Am. J. Physiol.* 256, H921 (1989); Swain, D. P. and Pittman, R. N., *Am. J. Physiol.* 256, H247–H255 (1989); Buerk, D. et al., *Microvasc. Res.*, 45:134–148 (1993)) (confirmed here) which promotes the T-structure in Hb. Raising the inspired oxygen concentration to 100% translates to periarteriolar $PO_2$s only as high as 40 mm Hg (Duling, B. and Berne, R. M. *Circulation Research*, 27:669 (1970); Popel, A. S., et al., (erratum *Am. J. Physiol.* 26(3) pt. 2). *Am. J. Physiol.* 256, H921 (1989); Swain, D. P. and Pittman, R. N. *Am. J. Physiol.* 256, H247–H255 (1989); Buerk, D. et al., *Microvasc. Res.*, 45:134–148 (1993)); i.e., breathing 100% $O_2$ may not fully maintain the R-structure in Hb in the microcirculation. Elimination of the periarteriolar $O_2$ gradient (artery-arteriole and arterial-venous difference in $PO_2$) is accomplished in hyperbaric chambers by applying 3 atmospheres of absolute pressure (ATA) while breathing 100% $O_2$ (Tibbles, P. M. and Edelsberg, J. S., *N. E. J. M.*, 334:1642–1648 (1996)).

Adult male Sprague-Dawley rats (290–350 g) were anesthetized with sodium pentobarbital (50 mg/kg IP), intubated and ventilated with a small animal respirator (Edco Scientific Inc., Chapel Hill, N.C.) at a rate and tidal volume to maintain normal values of $PaCO_2$ (35–45 mm Hg; $PaCO_2$= systemic arterial blood carbon dioxide tension). The femoral vein and artery were cannulated for infusion of drugs and for continuous monitoring of systemic blood pressure, respectively. Aliquots of arterial blood (200 $\mu$l) were drawn periodically to measure blood gas tensions and pH (Instrumentation Laboratory Co., model 1304 blood gas/pH analyzer). The blood was replaced intravenously with three volumes of normal saline. The inspired $O_2$ concentration was varied using premixed gases balanced with nitrogen. The tissue $PO_2$ was measured continuously with polarographic platinum microelectrodes (50 $\mu$m O.D. coated with hydrophobic gas permeable Nafion) implanted stereotaxically in both the right and left hippocampus (AP-3.4 mm, ML+2.2 mm), caudate putamen nucleus and substantia nigra (see coordinates below) (Young, W., *Stroke*, 11:552–564 (1980); Heiss, W. D. and Traupett, H., *Stroke*, 12:161–167 (1981); Dewhirst, M. W. et al., *Cancer Res.*, 54:3333–3336 (1994); Kerger, H. et al., *Am. J. Physiol.*, 268:H802–H810 (1995)). The $PO_2$ electrodes were polarized to -0.65V against a distant Ag/AgCl reference located on the tail and the current flow was measured using a low-impedance nA-meter. Regional arterial $PO_2$ was adjusted by changing the inspired $O_2$ concentration and atmospheric pressure.

Polarographic hydrogen ($H_2$)-sensitive microelectrodes were implanted stereotaxically in the substantia nigra (AP -5.3 mm, ML -2.4 mm to the bregma, depth 3.2 mm), caudate putamen nucleus (CPN) (AP +0.8 mm, ML -2.5 mm, depth 5.2 mm) and parietal cortex, for measurement of regional blood flow (Young, W., *Stroke*, 11:552–564 (1980); Heiss, W. D. and Traupett, H., *Stroke*, 12:161–167 (1981)). The microelectrodes were made from platinum wire and insulated with epoxy, with the exception of the tip (1 mm) which was coated with Nafion. For placement, the electrodes were mounted on a micromanipulator and the rat's head was immobilized in a Kopf stereotaxic frame. $H_2$-sensitive electrodes were polarized to +400 mV against a distant reference electrode on the tail, and the polarographic current was measured using a low-impedance nA meter during and after the inhalation of hydrogen gas (2.5%) for 1 min. Both the hydrogen clearance curves and voltage for oxygen measurements were made using PC WINDAQ (software, DI-200 AC, Dataq Instruments, Inc., Akron, Ohio). Cerebral blood flow was calculated using the initial slope method (Young, W., *Stroke*, 11:552–564 (1980); Heiss, W. D. and Traupett, H., *Stroke*, 12:161–167 (1981)). Regional blood flow responses were monitored for 30 min. prior to and 30 min. following drug administration; hemoglobins were given at time 0.

Blood was drawn from indwelling catheters in the carotid artery (arterial blood that perfuses the brain) and superior vena cava/right atrium (venous return to the heart) of 5 rats exposed first to room air (21% $O_2$) and then 100% $O_2$+3 ATA in a hyperbaric chamber. Levels of SNO-Hb and nitrosyl Hb (Hb[Fe]NO; FeNO in FIG. 9) were determined from these samples (by methods in Example 8) as a measure of SNO-Hb and nitrosyl Hb (Hb[Fe]NO) in blood that perfuses the brain. The mean $O_2$ saturation of venous blood (room air) was 69%; of arterial blood (room air) was 93%; of venous blood (100%+3 ATA) was also 93% and of arterial blood (100%+3 ATA) was 100% (FIG. 9). Numerous statistical comparisons were highly significant. For example, SNO-Hb venous 100% $O_2$+3 ATA vs. SNO-Hb venous 21% $O_2$, P=0.004; and nitrosyl Hb venous 21% $O_2$ vs. arterial 21% $O_2$ P=0.008. On the other hand, SNO-Hb and nitrosyl Hb were not different in artery 21% $O_2$ compared with venous 100%+3 ATA (which have identical $O_2$ saturations), nor did the differences reach significance between venous and arterial 100% $O_2$+3 ATA. n=5 for all measurements.

In 21% $O_2$, venous blood contained mostly nitrosyl Hb, whereas arterial blood contained significant amounts of SNO-Hb (FIG. 9). On the other hand, SNO-Hb predominated in both arterial and venous blood in 100% $O_2$+3 ATA (FIG. 9). In hyperbaric conditions, the tissues are oxygenated primarily by $O_2$ dissolved in plasma. Physiologically circumventing the unloading of $O_2$ by Hb alters the endogenous SNO/nitrosyl Hb balance. The data show that SNO-Hb appears to form endogenously in R-structure whereas SNO is released in the T-structure (compare venous 21% $O_2$ (T-state) with arterial 100% $O_2$+3 ATA (R-state)).

This structure-function relationship in vivo is consistent with both the in vitro pharmacology and the molecular model suggesting that 1) $O_2$ is an allosteric effector of Hb S-nitrosylation; 2) binding of NO to hemes of Hb is favored in the T-structure; (some of the NO released during arterial-venous (A-V) transit appears to be autocaptured at the hemes) and 3) maintaining endogenous SNO-Hb in the R-structure by eliminating the A-V $O_2$ gradient preserves levels of SNO (compare venous 100% $O_2$+3 ATA with arterial 21% $O_2$). Thus, it can be predicted that SNO-Hb should improve cerebral blood flow in 21% $O_2$, under which condition SNO is readily released during A-V transit, but not under the hyperoxic conditions that maintain the R-structure in artery and vein.

Example 12

$O_2$-Dependent Effects of SNO-Hb and Hb on Local Cerebral Blood Flow

The cerebrovascular effects of SNO-Hb were measured in adult male Sprague-Dawley rats using $O_2$ and $H_2$ (blood flow)-sensitive microelectrodes that were placed stereotaxically in several regions of the brain as for Example 11.

SNO-Hb increases blood flow under tissue hypoxia, whereas it decreases blood flow under hyperoxia. In contrast, Hb decreases blood flow irrespective of the $PO_2$. Comparative effects of SNO-Hb (●) and Hb (■) (1 μmol/kg infused over 3 minutes) on local blood flow in substantia nigra (SN), caudate putamen nucleus, and parietal cortex are shown for three different conditions. In 21% $O_2$, SNO-Hb improved blood flow in all three regions of the brain tested, whereas native Hb decreased local blood flow, paradoxically attenuating $O_2$ delivery to hypoxic tissues (FIGS. 10A, 10B and 10C; all curves are highly statistically significantly different from one another and from baseline by ANOVA). In rats breathing 100% $O_2$, where the periarteriolar $O_2$ gradient has been essentially eliminated, the increase in flow to SNO-Hb was significantly attenuated (i.e., only the SN increase reached statistical significance), but the Hb-mediated decrease in flow was preserved (FIGS. 10D, 10E and 10F; all curves remain different from one another by ANOVA to P<0.05). In 100% $O_2$+3 ATA, both SNO-Hb and Hb tended to decrease cerebral flow to similar extents (FIGS. 10G, 10H and 10I; curves are not different by ANOVA). S-nitrosoglutathione (GSNO) increased brain perfusion in 100% $O_2$ and 100% $O_2$+3 ATA, reversing protective vasoconstriction (not shown). Baseline blood flow was decreased by ~10% under 100% $O_2$+3 ATA as compared to 100% $O_2$. n=7 for all data points. Values of tissue/microvascular $PO_2$ ranged from 19–37 mm Hg in 21% $O_2$; from 68–138 mm Hg in 100% $O_2$; and from 365–538 mm Hg in 100%+3 ATA (Duke University Medical Center Hyperbaric Chambers).

SNO-Hb acts like native Hb (net NO scavenger) when it is in the R (oxy)-structure and like GSNO (net NO donor) in the T (deoxy)-structure. The results are consistent with the conclusion that SNO-Hb is a nitrosothiol whose vasoactivity is allosterically controlled by $PO_2$.

Example 13

Hemodynamics of Cell Free and Intraerythrocytic SNO-Hb, Hb and GSNO at Different $O_2$ Concentrations Rats were anesthetized by intraperitoneal injection of pentobarbital, and the femoral arteries and veins accessed by local cutdown. The artery was then cannulated and the blood pressure monitored continuously using a P23 XL pressure transducer (Viggo Spectramed, Oxnard, Calif.) attached to a Gould recorder. The femoral vein was used for infusion of drugs and red blood cells containing SNO-Hb (1 ml over 1 min.) and an IBM PC (WINDAQ 200, Dataq Instruments, Inc.; Akron, Ohio) was used for data acquisition.

Drugs were infused through the femoral vein at 1 μmol/kg infused over 1 minute after blood pressure had stabilized (approximately 30 min). Measurements shown (FIG. 11A) were taken at 10 min. post-infusion of drug. Similar responses were seen at 3 and 20 min. SNO-Hb produced significantly less of an increase in blood pressure than Hb (P<0.05), whereas GSNO decreased blood pressure. P<0.05 vs. SNO-Hb; *P<0.05, **P<0.01) vs. baseline blood pressure. n=5–6 for each drug.

Infusions of SNO-RBCs also lowered blood pressure consistent with a GSNO-like effect (FIG. 11B). SNO-RBCs produced dose-dependent hypotensive effects (similar to those of cell-free SNO-Hb) (P<0.001 at all points vs. baseline). The hypotensive effects of SNO-RBCs were potentiated by pre-administration of the NO synthase inhibitor $N^G$-monomethyl-L-arginine (L-NMMA; 50 mg/kg). n=8 for each data point. Curves different by ANOVA (P<0.01), *P<0.05 vs. L-NMMA. The amount of hemolysis in these experiments was trivial. Infusion of the hemolysate had no effect on blood pressure.

NO synthase inhibition increases tissue $O_2$ consumption by relieving the inhibition of mitochondrial respiration produced by NO in the tissues (King, C. E. et al., *J. Appl. Physiol.*, 76(3):1166–1171 (1994); Shen, W. et al., *Circulation*, 92:3505–3512 (1995); Kobzik, L. et al., *Biochem. Biophys. Res. Comm.*, 211 (2):375–381 (1995)). This should, in turn, increase the periarteriolar $O_2$ gradient which might explain some of the potentiation. However, other factors, such as a change in tone or distribution of blood flow imposed by L-NMMA, may well contribute. The effects of SNO-Hb on blood pressure are consistent with SNO being released in resistance arterioles to compensate for NO scavenging at the heme iron.

Example 14

Synthesis of S-Nitroso-Oxyhemoglobin (SNO-Hb [Fe(II)]O$_2$) and SNO-metHb (SNO-Hb[FeIII])

Hemoglobin (Hb)A$_o$ was purified from human red blood cells as previously described (Kilbourn, R. G. et al., *Biochem. Biophys. Res. Commun.*, 199:155–162 (1994)). HbA$_o$ was dialyzed against 20% borate, 0.5 mM EDTA (pH 9.2) at 4° C. for 12–16 hours. The oxyHb concentration was determined based on the optical absorbance at 577 nm (i.e., using the millimolar extinction coefficient 14.6).

Hb was reacted with 10-fold molar excess S-nitrosocysteine (CYSNO) which was synthesized with modification of standard procedure (see, for example, Stamler, J. S. and Feelisch, M., "Preparation and Detection of S-Nitrosothiols," pp. 521–539 in *Methods In Nitric Oxide Research* (M. Feelisch and J. S. Stamler, eds.), John Wiley & Sons Ltd., 1996) as follows. L-cysteine hydrochloride (1.1 M) dissolved in 0.5 N HCl/0.5 mM EDTA was reacted with an equal volume of 1 M NaNO$_2$ (sodium nitrite) dissolved in water, to form CYSNO (the ratio of cysteine to nitrite influences the SNO-Hb product and activity profile). The concentration of CYSNO was then adjusted by dilution in 200 mM phosphate buffer (PBS), pH 8.0, to yield a working CYSNO solution (pH 6–7). This was then reacted at room temperature with a 20-fold volume excess of Hb (in borate, pH 9.2), resulting in a final 10-fold molar excess of CYSNO over Hb (ratio influences product critically). Following the incubation (periods determined by the desired synthetic preparation; i.e., a desired ratio of SNO/tetramer; desired met- to oxy- to nitrosyl-Hb ratios; polynitrosated or non-polynitrosated; for example, 10 min. preferred time for SNO-oxyHb with 2 SNO per tetramer; see below), the reaction mixture was rapidly added to a column of fine Sephadex G-25 (20 to 30-fold volume excess over the reaction mixture) preequilibrated with 100 mM PBS pH 7.4, 0.5 mM EDTA. Typically, a 150 µl sample of the mixture was added to a 4.5 ml column measuring 12 mm (inner diameter). The column was then centrifuged at 1200 g for 60 seconds and the effluent collected in a 1.5 ml airtight plastic vial that was subsequently kept on ice and protected from light.

Spectrophotometric determination of total Hb and S-nitrosothiol (SNO) concentration was determined by Saville assay (especially modified from standard protocol (see Materials and Methods section of Exemplification; see also, for example, Stamler, J. S. and Feelisch, M., "Preparation and Detection of S-Nitrosothiols," pp. 521–539 in *Methods In Nitric Oxide Research* (M. Feelisch and J. S. Stamler, eds.) John Wiley & Sons Ltd., 1996; Saville, B., *Analyst*, 83:670–672 (1958)) by keeping the Hb in the sample to 5 µl per 50 µl sample volume added to assay, adding 0.1–1 Tween as necessary, and by correcting for nitrosyl Hb content converted to nitrite).

Incubations of CYSNO with HbA resulted in different synthetic products (and different activities) over time. For example, with 10 min incubations, the Hb preparation contains 1.857±0.058 SNO groups per tetramer, and is approximately 12–15% metHb and 1–3% nitrosyl(FeII)-hemoglobin. (Capillary electrophoretic analysis actually reveals a mixture of three protein peaks.) MetHb was then reduced (lowered from 130% to 20% with 100-fold excess NaCNBH$_3$ (dissolved in PBS, pH 8.0) under anaerobic conditions (achieved by purging with argon gas for a minimum of 10 minutes) for 5 minutes. (Lower concentrations of NaCNBH$_3$ or treatment of the samples under aerobic conditions were not effective in lowering the metHb concentration, and alternative measures to reduce the heme result in SNO reduction.) The resulting mixture was rapidly added to a column of fine Sephadex G-25 (20 to 30-fold volume excess) preequilibrated with 100 mM PBS pH 7.4, 0.5 mM EDTA. The final S-nitrosothiol/Hb tetramer ratios were not significantly different from those measured in samples degassed and treated with PBS only: losses in SNO/Hb ratio relative to the starting ratios were consistent with the expected time-dependent decay of SNO-deoxyHb and could be reduced to an insignificant loss by taking preparitive time into consideration. NaCNBH$_3$ treatment of a sample with a mean SNO/Hb ratio of ~1 decreased the metHb content from 5.6% to 0.63%. Nitrosyl(FeII)-hemoglobin and metHb contamination of SNO-oxyHb preparations of ~2% are acceptable, inasmuch as they do not seem to alter bioactivity of SNO-oxyHb, and enable O$_2$ binding measurements, that is, P$_{50}$, determinations (so called SNO-Hb[Fe(II)]O$_2$). By the same token, bioactivity can be modified and varied by controlling the proportion of SNO-metHb (high and low spin) and nitrosyl(FeII)-hemoglobin in the preparation. The spin state of metHb can be controlled by the heme ligand: cyan-metHb is low spin and aquo-met Hb (H$_2$O bound as ligand) is high spin; nitrosyl Hb ratios are made depending on the desired result. High yield SNO-metHb, SNO-nitrosyl(FeII)-hemoglobin (or SNO-carboxyl Hb) can be formed by using the heme-liganded protein as starting material. Carboxyl Hb can be made by gassing Hb with CO under anaerobic conditions. HbCO can then be used as starting material; likewise, various combinations of Hb[FeNO][FeCO] can be used as starting material.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method for reducing blood pressure in a mammal comprising the steps of:
   a) isolating the mammal's red blood cells;
   b) treating the mammal's red blood cells with a solution comprising S-nitrosocysteine, S-nitrosohomocysteine or S-nitrosocysteinylglycine; and
   c) readministering to the mammal the red blood cells.

2. A method for reducing blood pressure in a first human comprising the steps of:
   a) isolating red blood cells of a second human;
   b) treating the red blood cells with a solution comprising S-nitrosocysteine, S-nitrosohomocysteine or S-nitrosocysteinylglycine, thereby obtaining treated red blood cells; and
   c) administering to the first human the treated red blood cells.

3. A method for reducing blood pressure in a mammal, comprising administering red blood cells treated with a solution comprising S-nitrosocysteine, S-nitrosohomocysteine or S-nitrosocysteinylglycine to the mammal.

4. The method of claim 1 wherein the red blood cells are treated with a solution comprising S-nitrosohomocysteine.

5. The method of claim 1 wherein the mammal is a human.

6. The method of claim 3 wherein the red blood cells are treated with a solution comprising S-nitrosocysteine.

7. The method of claim 3, further comprising administering a nitric oxide synthase inhibitor to the mammal.

8. A method for reducing blood pressure in a mammal, comprising administering to the mammal a blood substitute comprising red blood cells treated with a solution compris ing S-nitrosocysteine, S-nitrosohomocysteine or S-nitrosocvsteinylglycine.

9. A method for reducing blood pressure in a human, comprising administering red blood cells treated with a solution comprising S-nitrosocysteine to the human.

10. A method for reducing blood pressure in a human, comprising administering red blood cells treated with a solution comprising S-nitrosohomocysteine to the human.

11. A method for reducing blood pressure in a human, comprising administering red blood cells treated with a solution comprising S-nitrosocysteinylglycine to the human.

* * * * *